(12) United States Patent
Schafer et al.

(10) Patent No.: US 8,372,081 B1
(45) Date of Patent: Feb. 12, 2013

(54) VERTEBRAL DISTRACTION ASSEMBLY AND RELATED METHODS

(75) Inventors: Andrew Schafer, Ramona, CA (US); Rob German, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 493 days.

(21) Appl. No.: 12/378,936

(22) Filed: Feb. 20, 2009

Related U.S. Application Data

(60) Provisional application No. 61/029,953, filed on Feb. 20, 2008.

(51) Int. Cl.
*A61B 17/66* (2006.01)

(52) U.S. Cl. ............. 606/90; 606/57; 606/282; 606/105

(58) Field of Classification Search ................... 606/90, 606/105, 57, 282; 269/43, 172, 177, 243, 269/225, 61; 76/79.5; 72/457; 600/215, 600/221
See application file for complete search history.

(56) References Cited

U.S. PATENT DOCUMENTS

| | | | | |
|---|---|---|---|---|
| 351,151 | A * | 10/1886 | Beachman | 29/560.1 |
| 608,268 | A * | 8/1898 | Pelton | 100/111 |
| 1,812,585 | A * | 6/1931 | Collins | 269/59 |
| 2,114,637 | A * | 4/1938 | Olsen | 269/84 |
| 4,187,841 | A * | 2/1980 | Knutson | 606/105 |
| 4,386,603 | A * | 6/1983 | Mayfield | 606/105 |
| 4,566,466 | A | 1/1986 | Ripple et al. | |
| 4,611,582 | A * | 9/1986 | Duff | 606/258 |
| 4,733,657 | A * | 3/1988 | Kluger | 606/57 |
| 4,991,566 | A * | 2/1991 | Shulman et al. | 600/213 |
| 5,052,373 | A * | 10/1991 | Michelson | 600/217 |
| 5,074,864 | A * | 12/1991 | Cozad et al. | 606/54 |
| 5,207,676 | A * | 5/1993 | Canadell et al. | 606/54 |
| 5,330,474 | A * | 7/1994 | Lin | 606/267 |
| 5,393,036 | A * | 2/1995 | Sheridan | 254/100 |
| 5,431,658 | A * | 7/1995 | Moskovich | 606/99 |
| 5,616,117 | A * | 4/1997 | Dinkler et al. | 600/232 |
| 5,725,526 | A * | 3/1998 | Allard et al. | 606/57 |
| 5,797,909 | A | 8/1998 | Michelson | |
| 6,096,038 | A | 8/2000 | Michelson | |
| 6,159,215 | A | 12/2000 | Urbahns et al. | |
| 6,332,887 | B1 * | 12/2001 | Knox | 606/87 |
| 6,478,800 | B1 | 11/2002 | Fraser et al. | |
| 6,749,613 | B1 * | 6/2004 | Conchy et al. | 606/57 |
| 7,011,658 | B2 * | 3/2006 | Young | 606/258 |
| 7,578,822 | B2 * | 8/2009 | Rezach et al. | 606/90 |
| 8,211,149 | B2 * | 7/2012 | Justis | 606/258 |
| 2005/0165408 | A1 | 7/2005 | Puno et al. | |
| 2007/0093828 | A1 | 4/2007 | Abdou | |
| 2008/0255567 | A1 * | 10/2008 | Accordino | 606/90 |
| 2008/0311542 | A1 * | 12/2008 | Rana et al. | 433/140 |

* cited by examiner

*Primary Examiner* — Kevin T Truong
*Assistant Examiner* — Zade Coley
(74) *Attorney, Agent, or Firm* — Jonathan Spangler; Rory Schermerhorn

(57) ABSTRACT

A spinal distraction assembly is provided for distracting the disc space between a pair of vertebrae, the vertebrae each having been implanted with a bone anchor. The spinal distraction assembly includes a first anchor engaging element and a second anchor engaging element. The first anchor engaging element includes a body having a channel extending through the longitudinal axis of the body. The second anchor engaging element includes a guide bar. The guide bar is dimensioned to translate through the body channel. Anchor engaging arms extend laterally from each of the body and guide bar.

20 Claims, 20 Drawing Sheets

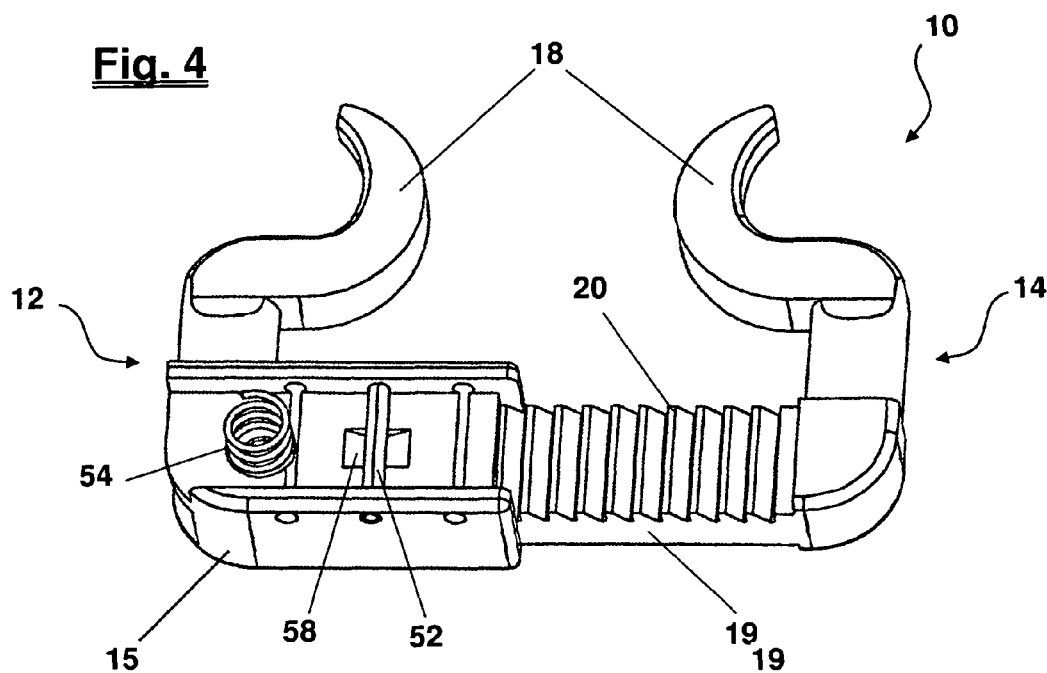
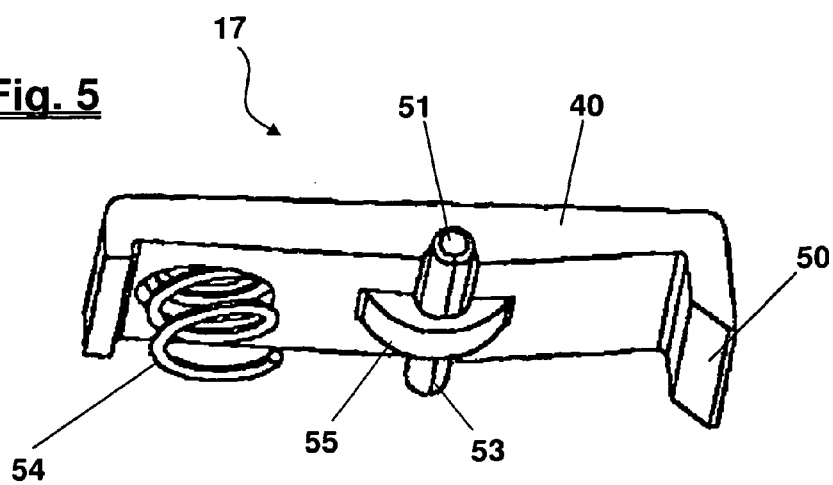

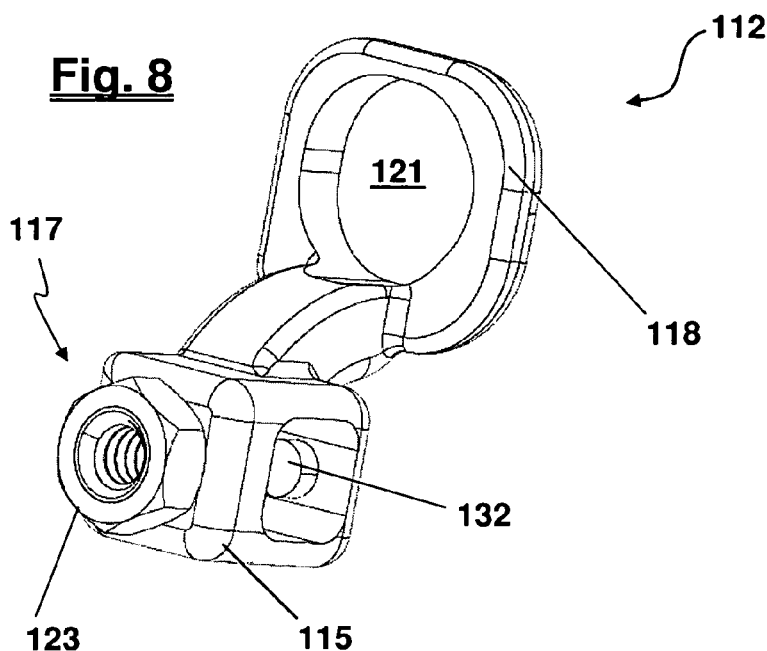
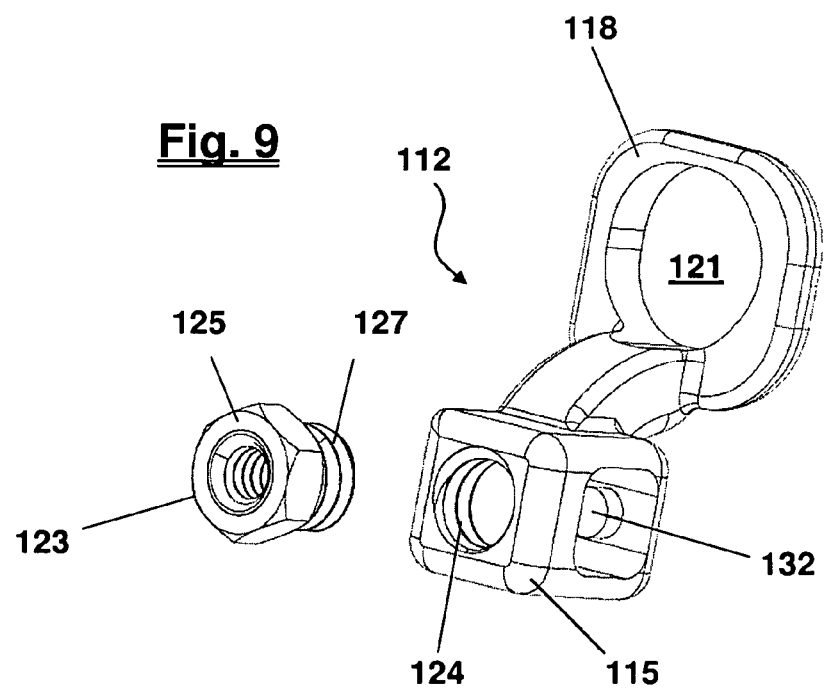

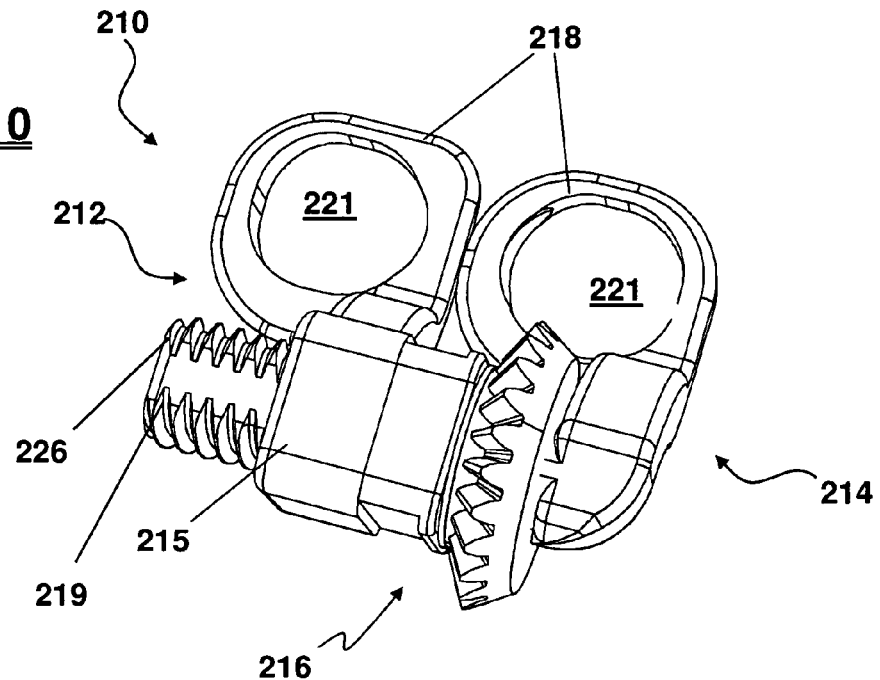
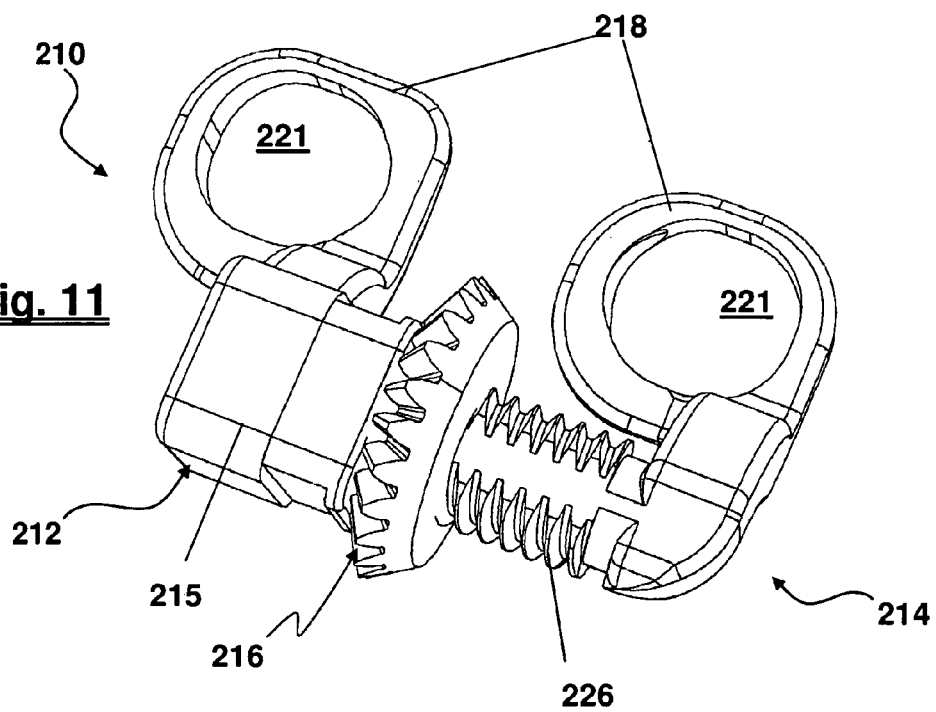

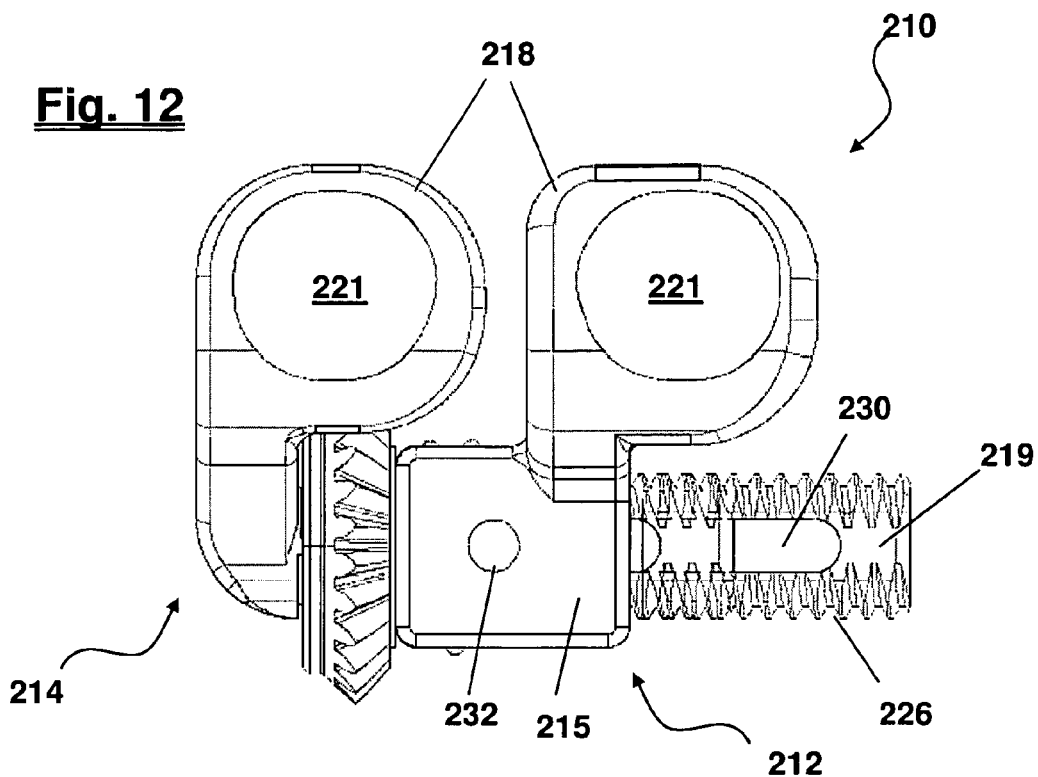
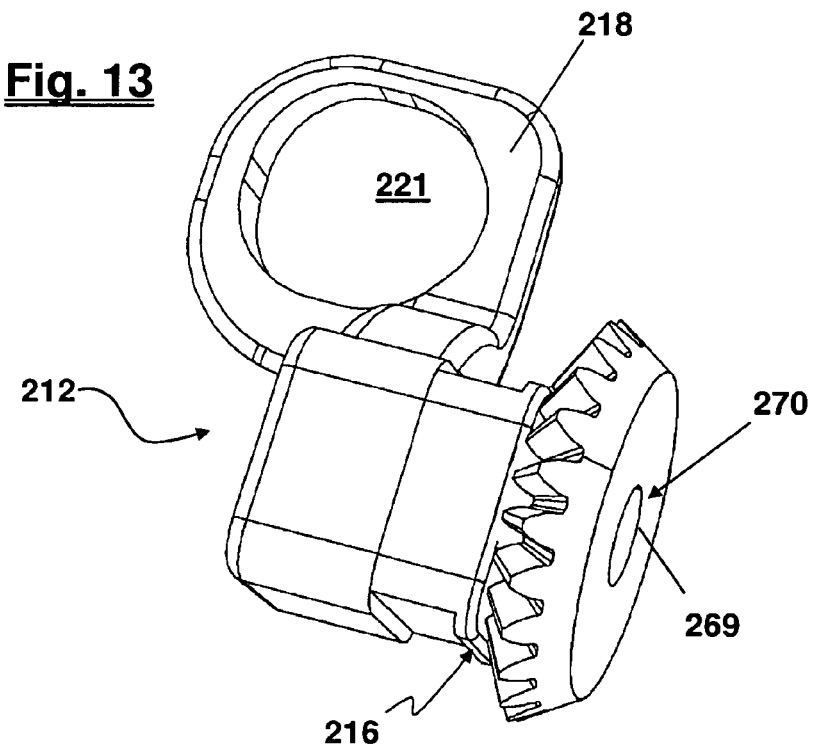

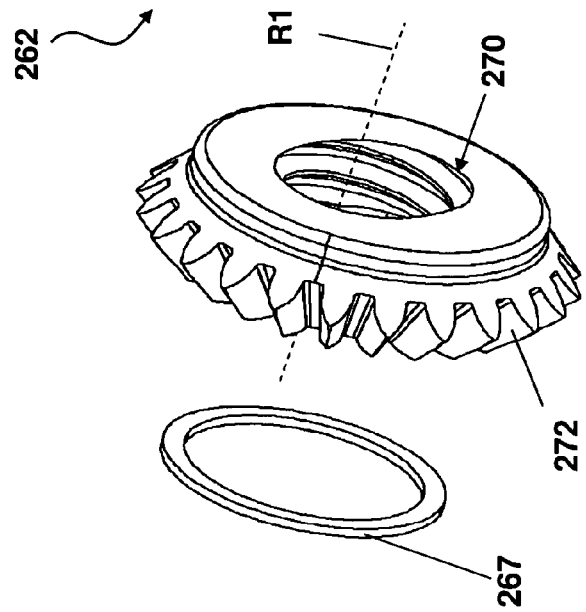
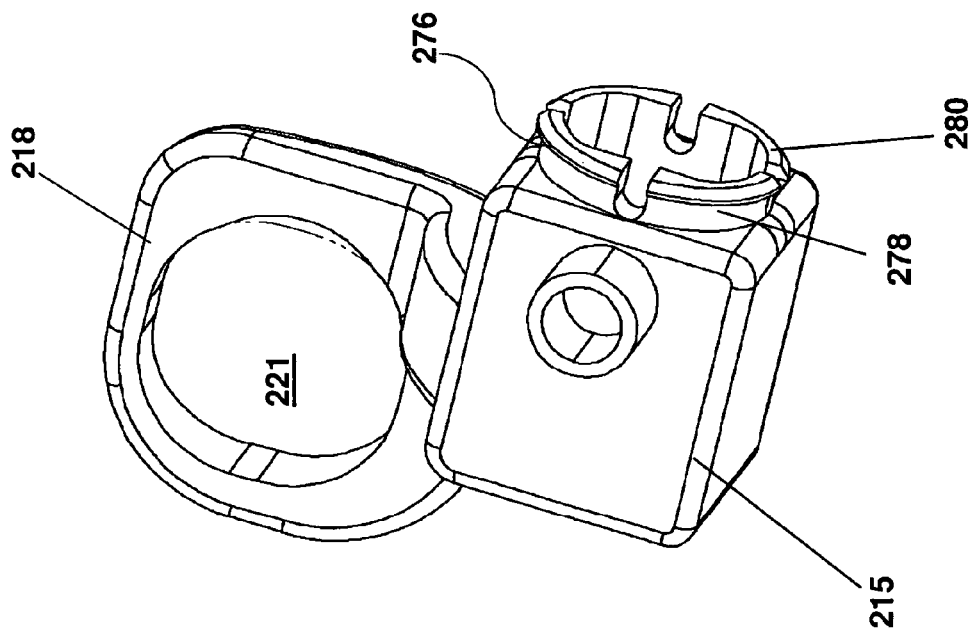
Fig. 14

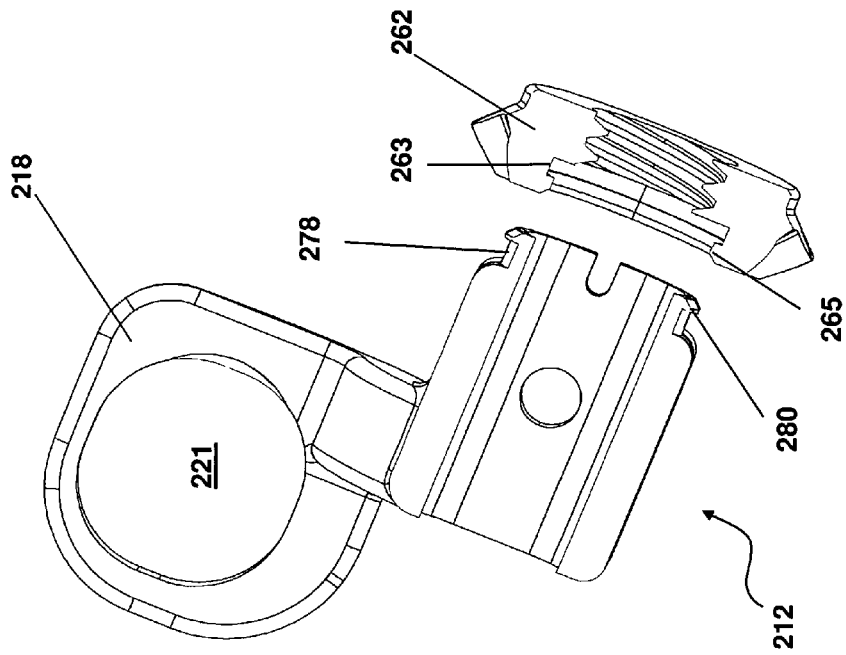
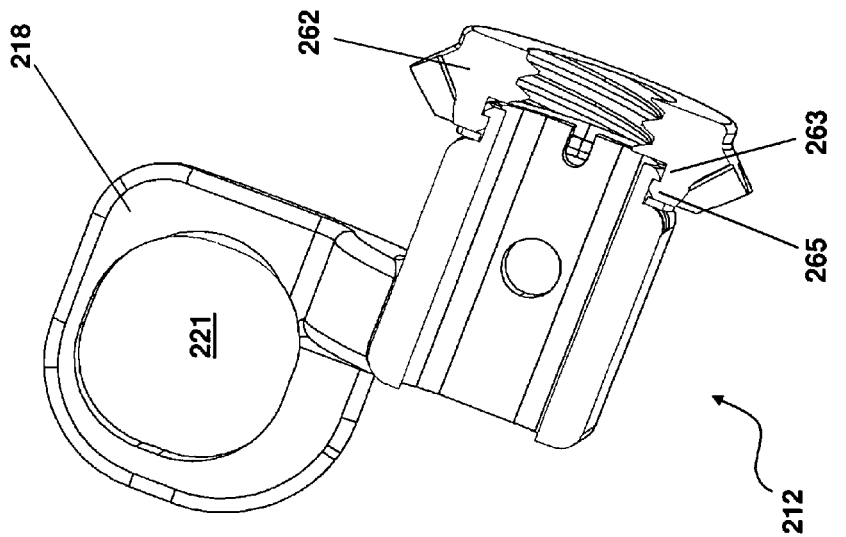

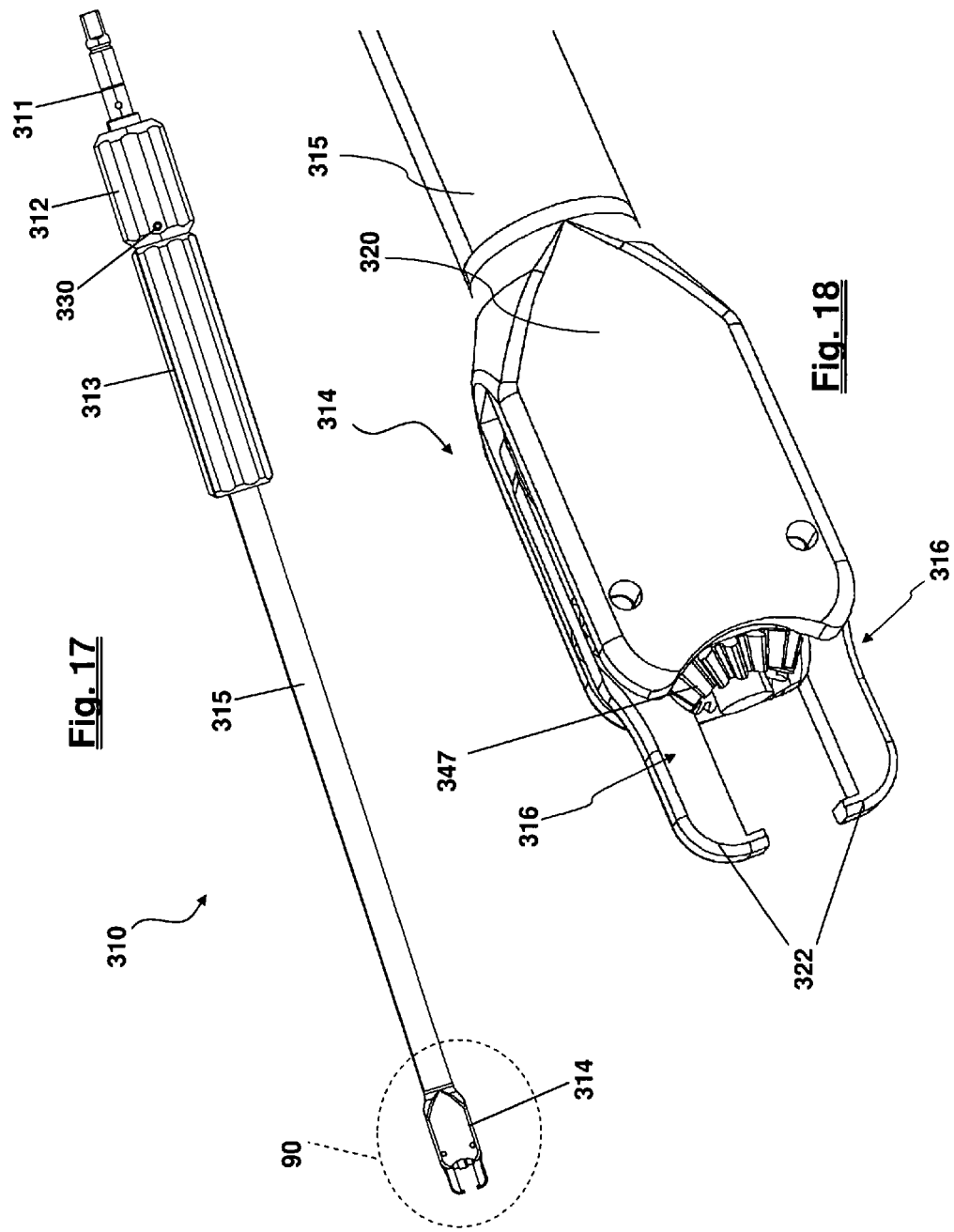

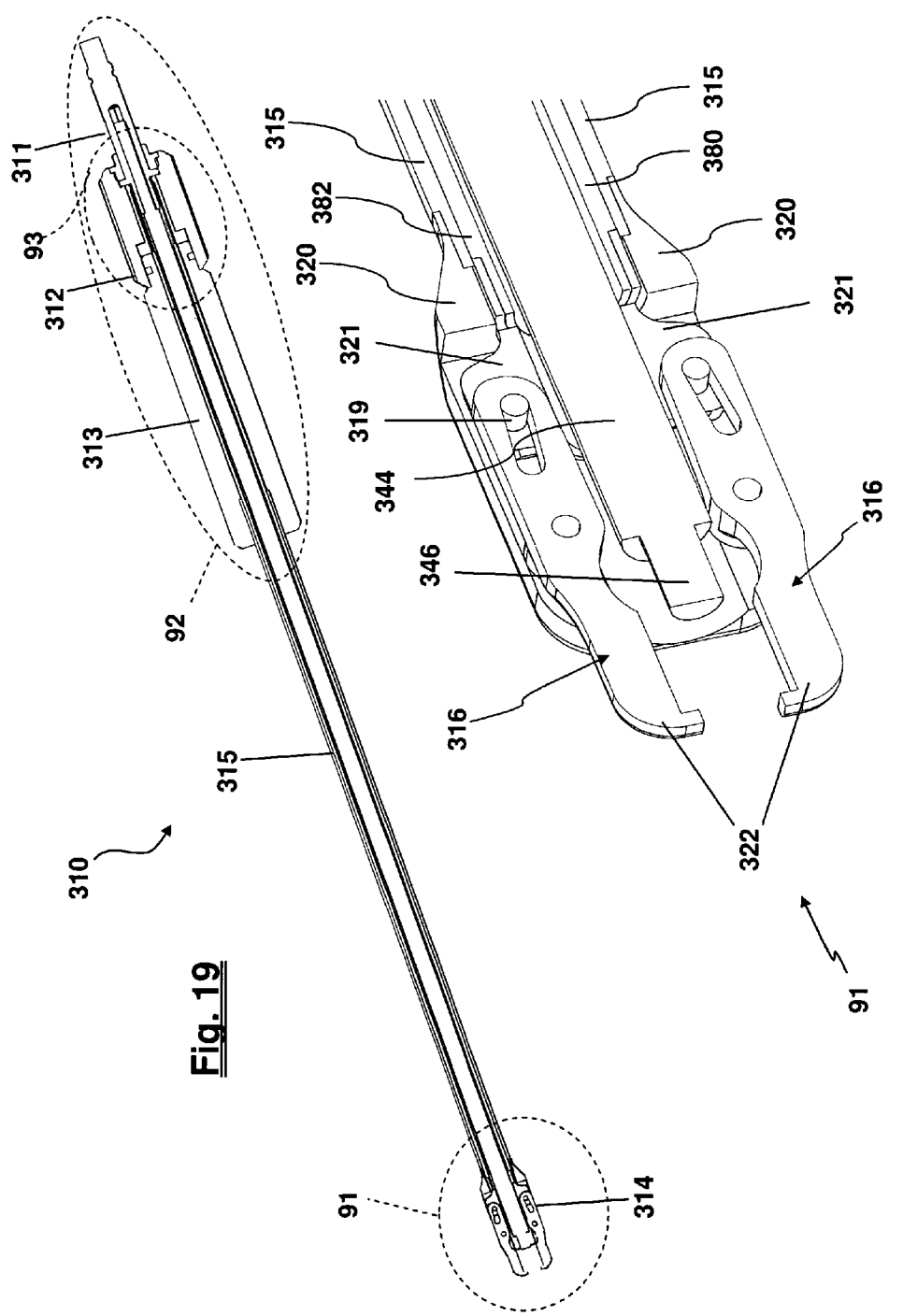

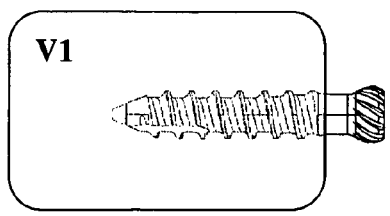
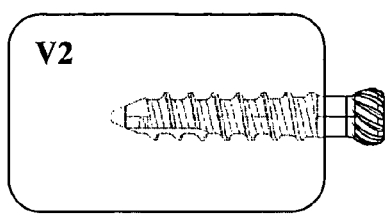
Fig. 25A
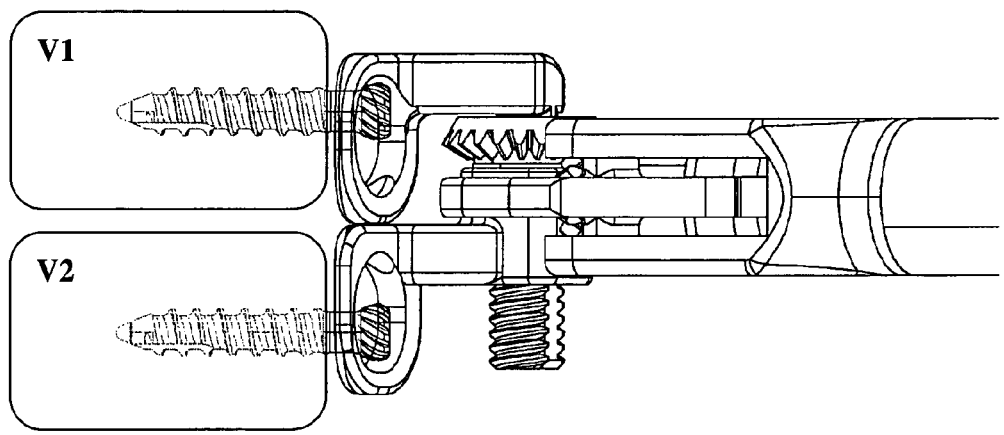
Fig. 25B

VERTEBRAL DISTRACTION ASSEMBLY AND RELATED METHODS

CROSS-REFERENCE TO RELATED APPLICATIONS

This application is a non-provisional patent application claiming the benefit of priority under 35 U.S.C. §319(e) from U.S. Provisional Patent Application Ser. No. 61/029,953, filed on Feb. 20, 2008, the entire contents of which is hereby expressly incorporated by reference into this disclosure as if set forth fully herein.

FIELD

The present invention relates generally to a distraction device and methods for adjusting the spacing between spinal vertebrae during surgery.

BACKGROUND

The spinal column is a highly complex system of bones and connective tissues that provides support for the body and protects the delicate spinal cord and nerves. The spinal column includes a series of vertebral bodies stacked one atop the other, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies.

There are many types of spinal column disorders including scoliosis (abnormal lateral curvature of the spine), kyphosis (abnormal forward curvature of the spine), excess lordosis (abnormal backward curvature of the spine), spondylothesis (forward displacement of one vertebra over another), and other disorders caused by abnormalities, disease or trauma, such as ruptured or slipped discs, degenerative disc disease, fractured vertebra, and the like. Patients that suffer from such conditions usually experience extreme and debilitating pain, as well as diminished nerve function.

Surgical techniques commonly referred to as spinal fixation use surgical implants for fusing together and/or mechanically immobilizing two or more vertebral bodies of the spinal column. Spinal fixation may also be used to alter the alignment of adjacent vertebral bodies relative to one another so as to change the overall alignment of the spinal column. Such techniques have been used effectively to treat the above-described conditions and, in most cases, to relieve pain. Often times it is necessary to distract the disc space between adjacent vertebrae in order to perform the appropriate surgical procedure.

While various distraction systems for distracting a disc space between vertebrae are currently available, there nonetheless exists a need for other manners of providing sufficient distraction between adjacent vertebrae during surgical procedures.

SUMMARY

A spinal distraction assembly is provided for distracting the disc space between a pair of vertebrae, the vertebrae each having been implanted with a bone anchor. The spinal distraction assembly includes a first anchor engaging element and a second anchor engaging element. The first anchor engaging element includes a body having a channel extending through the longitudinal axis of the body. The second anchor engaging element includes a guide bar. The guide bar is dimensioned to translate through the body channel. Anchor engaging arms extend laterally from each of the body and guide bar.

The first anchor engaging element and the second anchor engaging element interconnect so that the body of the first anchor engaging element receives the guide bar of the second anchor engaging element therethrough. The body is movable along the guide bar to either expand (distract) or contract (compress) the distance between the anchor engaging arms. When the anchor engaging arms are engaged with anchors implanted in a pair of vertebral bodies, operating the distraction assembly to expand the distance between the anchor engaging arms will distract the disc space between the vertebral bodies. Likewise, operating the distraction assembly to contract the distance between the anchor engaging arms when the arms are engaged with anchors implanted in a pair of vertebral bodies, the disc space between the bodies will be compressed.

The first anchor engaging element and the second anchor engaging element each include an anchor engaging arm that extends laterally away from the body and guide bar, respectively. The anchor engaging arms may terminate in looped ends with apertures intended to receive the anchor elements therethrough. According to one example, the apertures may be dimensioned to advance over the shaft of an anchor element, such as for example, a pedicle screw. Additionally, the apertures may be dimensioned such that they may be advanced over the receiver member of a pedicle screw. The anchor engaging arms may also terminate in various other shaped ends. For example the arm ends may be hooks intended to engage the shaft of the bone anchor.

In some examples the spinal distraction assembly may include a locking mechanism. In one embodiment the locking mechanism includes a one way ratchet. The guide bar may include a series of teeth along the longitudinal axis. A pawl may be provided to engage the teeth on the guide bar. The pawl and teeth may be configured such that movement in on direction is permitted and movement in a second direction is prevented. The locking mechanism may be biased to automatically engage. The locking mechanism may also include a set screw configured advance through an aperture in the body and engage the guide bar. The locking mechanism may provide for one way locking or for two way locking.

In some examples the spinal distraction assembly may include an adjuster. The adjuster may be operable to move the body from one position to another position along the guide bar. According to one example, the adjuster may be generally ring shaped and includes an inner bore. The inner bore may be disposed about the guide bar. The interior surface of the inner bore may include threading complementary exterior threading on the guide bar such that rotation of the adjuster causes the adjuster to translate along the longitudinal axis of the guide bar. The adjuster may be coupled to the body such that the adjuster longitudinally fixed relative to the body is freely rotatable relative to the body. Thus, as the adjuster is rotated about the guide bar the adjuster moves longitudinally along the guide bar and drives the body along the guide bar in the same direction.

The distraction assembly may include a transition wheel to impart rotational force to the adjuster. The transition wheel may be attached to the body and may interconnect with the adjuster. The transition wheel and the adjuster may be configured such that rotation of the transition wheel imparts rotation to the adjuster.

Instruments may be provided for delivering the spinal distraction assembly and for imparting rotation to the adjuster. In one example, an instrument is provided with a pair of engagement arms. The engagement arms are linked to an intermediate handle that is operable to close the engagement arms about the body to securely grip the distraction assembly. The instruments may also include a driver. The driver may be linked to a proximal handle that is operable to rotate the driver about the longitudinal axis of the shaft of the instrument to rotate the adjuster. The driver may engage the transition wheel such that the driver rotates the transition wheel and the transition wheel rotates the adjuster.

The spinal distraction assembly may be used to distract a disc space between a pair of vertebrae during surgery by; a) affixing vertebral anchoring members, such as bone screws, into the adjacent vertebrae to be distracted; b) inserting the spinal distraction assembly to a position proximate to the vertebral anchoring members; c) engaging each anchor engaging arms to the corresponding anchor members; and d) applying a force to the anchor engaging arms. The force may be applied by imparting a rotational force to an adjuster. Applying the force to the anchor engaging arms will applies a distraction force to the bone anchor members, separating the vertebrae to the desired position.

BRIEF DESCRIPTION OF THE DRAWINGS

The invention will be more fully understood from the following detailed descriptions taken in conjunction with the accompanying drawings, in which:

FIG. 4 is a perspective view of the vertebral distraction assembly of FIG. 1 shown with a locking member removed to illustrate the interior;

FIG. 5 is a perspective view of a locking mechanism shown separated from the vertebral distraction assembly of FIG. 1;

FIG. 8 is a perspective view of a first anchor engaging element of the vertebral distraction assembly of FIG. 7;

FIG. 9 is perspective view of the first anchor engaging element of FIG. 8 with a set screw removed to illustrate the body aperture;

FIG. 10 is a perspective view of a vertebral distraction assembly according to another example embodiment;

FIG. 11 is a perspective view of the vertebral distraction assembly of FIG. 10 with an anchor engaging arm having been advanced to a more distracted position;

FIG. 12 is a bottom view of the vertebral distraction assembly of FIG. 10;

FIG. 13 is a perspective view of a first anchor engaging element of the vertebral distraction assembly of FIG. 10;

FIG. 14 is an exploded view of the first anchor engaging element of FIG. 13;

FIG. 15 is a cross-section view of the first anchor engaging element of the distraction assembly of FIG. 10;

FIG. 16 is a cross section view of the first anchor engaging element of FIG. 15 with a guide bar wheel shown separated from the body portion;

FIG. 17 is a side view of a distraction tool for use with the vertebral distraction assembly of FIG. 10, according to one example embodiment;

FIG. 18 is a perspective view of the distal end of the distraction tool of FIG. 17;

FIG. 19 is a cross-section view of the distraction tool of FIG. 17;

FIG. 20 is a perspective cross-section view of the distal end of the distraction tool of FIG. 17;

FIGS. 25A-25G illustrate steps for utilizing the spinal distraction assembly of FIG. 10 during a surgical procedure, according to one example method.

DETAILED DESCRIPTION

Figure 1:
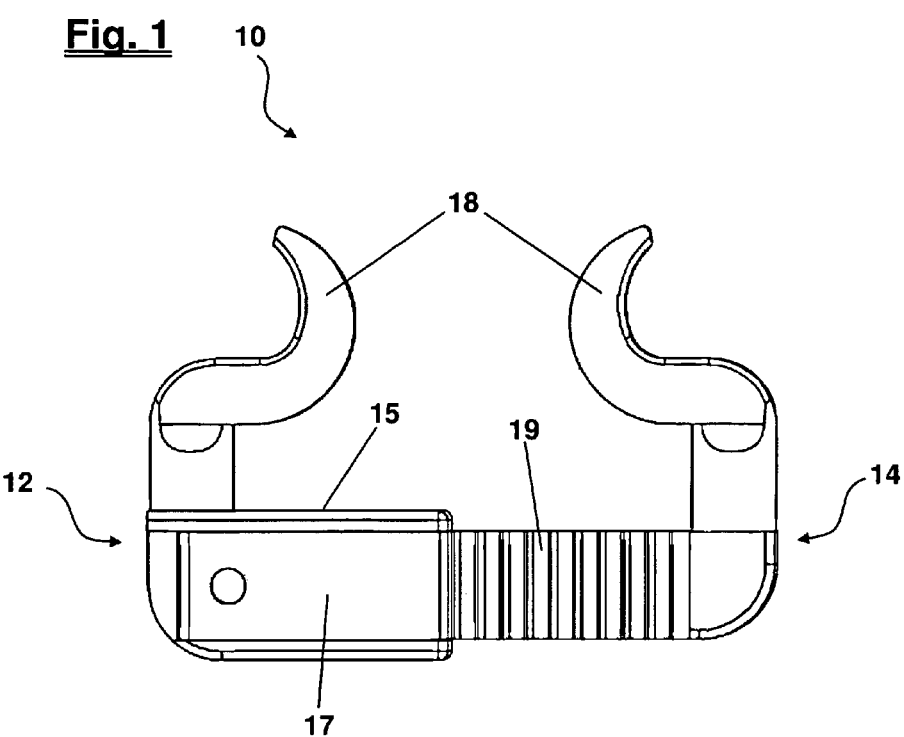
FIG. 1 is a top view of a vertebral distraction assembly according to one example embodiment.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal distraction assembly and related methods disclosed herein boasts a variety of inventive features and components that warrant patent protection, both individually and in combination.

With reference to FIGS. 1-5, a first example embodiment of a spinal distraction assembly 10 includes a first anchor engaging element 12 and a second anchor engaging element 14. First anchor engaging element 12 includes a body 15 having a channel extending through the longitudinal axis of the body and the second anchor engaging element 14 includes a guide bar 19. Guide bar 19 is dimensioned to translate through the body channel. Anchor engaging arms 18 extend approximately 90° laterally from each of the body 15 and guide bar 19. Attached to the body 15 of the first anchor engaging element 12 is a locking element 17 configured to engage the guide bar 19 and lock the position of body 15 relative to guide bar 19.

As assembled, the first anchor engaging element 12 and the second anchor engaging element 14 interconnect so that the body 15 of the first anchor engaging elements receives the guide bar 19 of the second anchor engaging element 14 therethrough. The body 15 is movable along the guide bar 19 to either expand (distract) or contract (compress) the distance between the anchor engaging arms 18. When the anchor engaging arms 18 are engaged with anchors implanted in a pair of vertebral bodies, operating the distraction assembly 10 to expand the distance between the anchor engaging arms will distract the disc space between the vertebral bodies. Likewise, operating the distraction assembly 10 to contract the distance between the anchor engaging arms 18 when the arms 18 are engaged with anchors implanted in a pair of vertebral bodies, the disc space between the bodies will be compressed.

Figure 2:
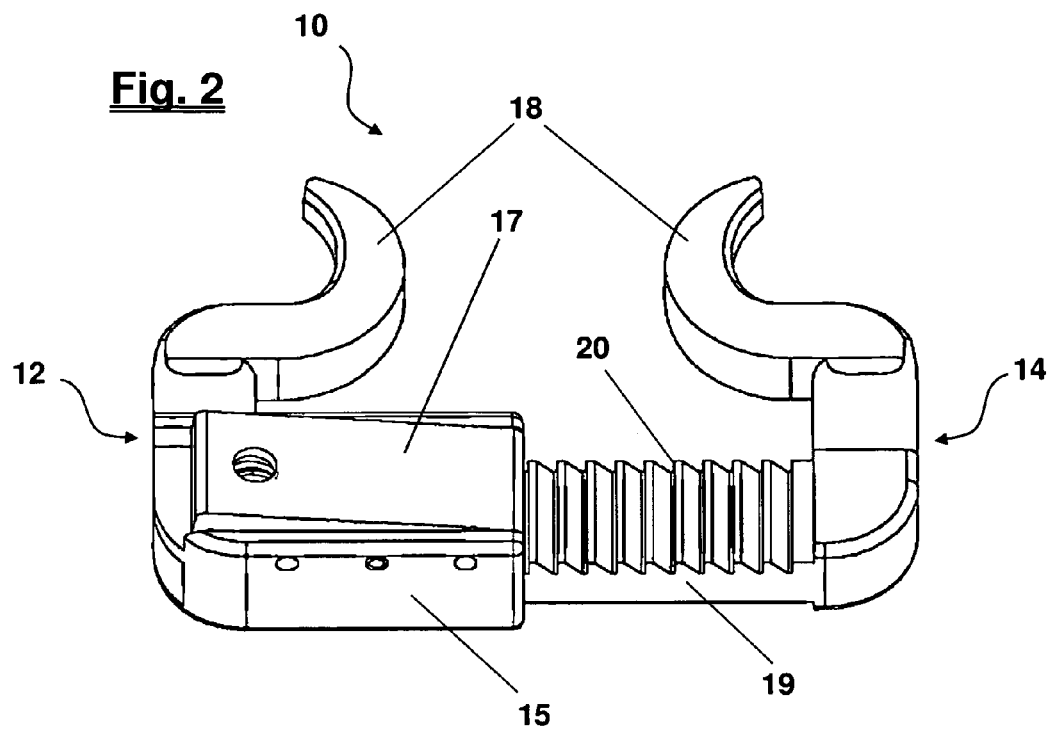
FIG. 2 is a perspective view of the vertebral distraction assembly of FIG. 1.

As shown in FIG. 2, by way of example only, the guide bar 19 may be generally rectangular and have angled teeth 20 situated along the top surface that permit movement in only a single (distracting) direction when the locking element 17 is engaged, as will be described in greater detail below. Although guide bar 19 is described in the present embodiment as having a generally rectangular shape configured to fit within body 15, other suitable configurations are also possible, for example, the guide bar 19 can be generally cylindrical, with angled teeth around at least a portion of the convex surface, and the body 15 can be generally cylindrical with a hollow interior that the guide bar 19 can slide through.

Figure 3:
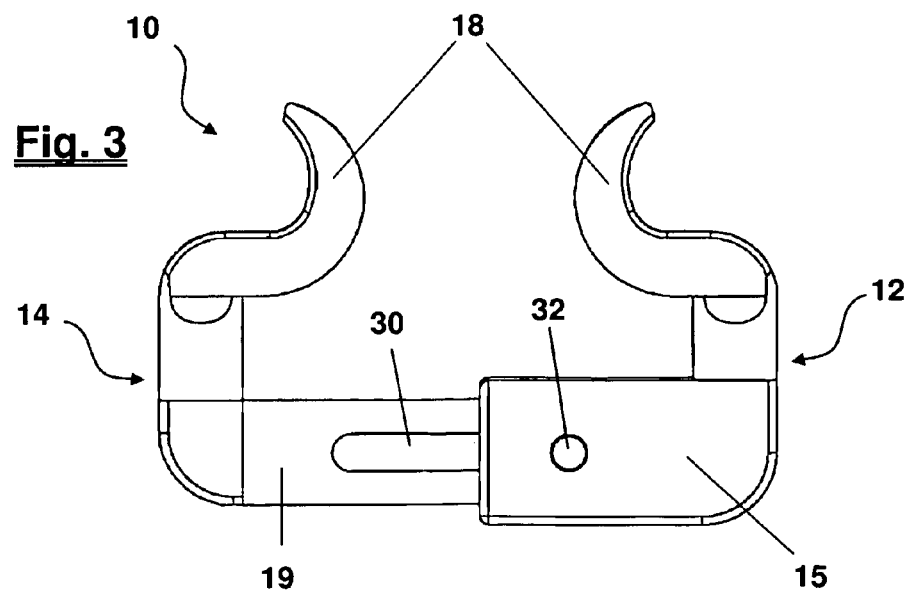
FIG. 3 is a bottom view of the vertebral distraction assembly of FIG. 1.
Figure 6:
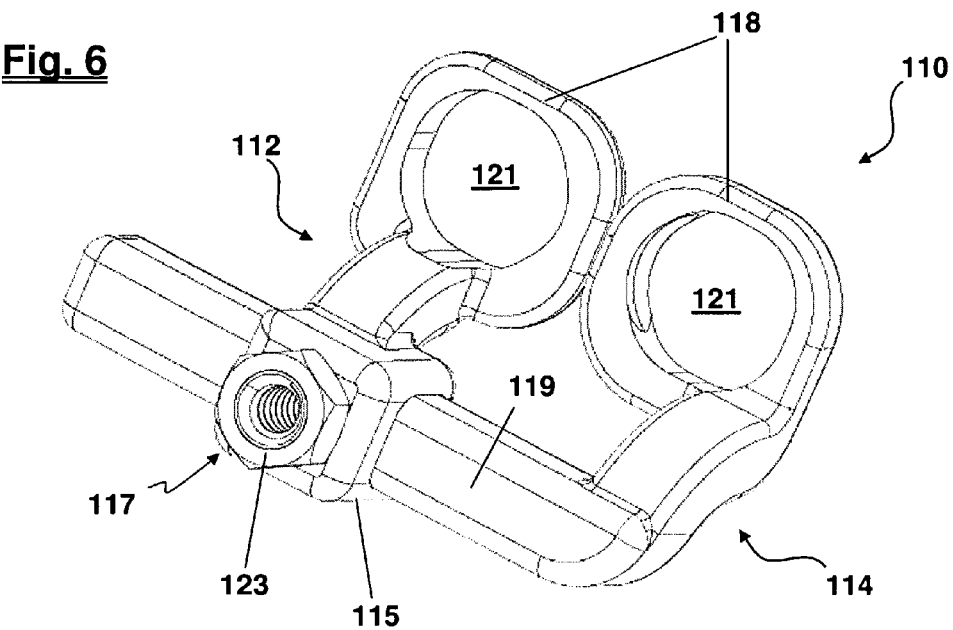
FIG. 6 is a perspective view of a vertebral distraction assembly, according to another example embodiment.

The bottom of the guide bar 19, as depicted by way of example in FIG. 3, includes a groove 30 that runs lengthwise along the longitudinal axis of the guide bar 19, stopping short of the end such that the groove is contained within the guide bar. A protuberance 32 on the body 15 projects inward into the groove 30 such that the body 15 is prevented from sliding off the guide bar 19 and separating from the second anchor engaging element 14. The maximum distraction distance of the distraction assembly 10 is thus controlled by the length of the guide bar 19, and particularly the length of the slot 30 and should be appreciated that the length of guide bar 19 and groove 30 may be varied according to any number of suitable configurations without departing from the scope of the present invention.

The first anchor engaging element 12 and the second anchor engaging element 14 each include an anchor engaging arm 18 that extends laterally at a generally 90° angle away from the body 15 and guide bar 19, respectively. As shown in this example embodiment, the anchor engaging arms 18 terminate in a hooked end intended to engage an anchor positioned on the vertebral body, such as a bone screw. Although anchor engaging arms 18 are described as terminating in a hooked end, other configurations of the anchor engaging arms 18 may also be suitable. For example, the anchor engaging arms 18 may terminate in a looped ends intended to fit over a vertebral anchor, or anchor engaging arms 18 can terminate in a cup-shaped ends intended to receive the vertebral anchor therein.

Best depicted in FIGS. 4-5, the locking element 17 inhibits return movement (contraction) of the body 15 along guide bar 19 to maintain a desired level of distraction until the locking element is released. The locking element 17 includes a locking member 40 and a spring 54. At approximately the midpoint, the bottom of the locking member 40 includes a crescent body 55 and a tube 53 extending transversely to the crescent body between sides of the locking member 40. The crescent body 55 rests within a concave groove 58 in the body 15 and a crossbar 52 passes through a lumen 51 of the tube 53 to moveably fix the locking member 40 to the body 15. The crescent body 55 and tube 53 act as a fulcrum about which the locking member 40 may pivot. The spring 54 is located at one end of the locking member 40. At the other end, the locking member 40 has a pawl 50 for engaging guide bar teeth 20. When the locking member 40 is in a neutral position spring 54 imparts an upward force on the end of the locking member 40 opposite the pawl 50, causing the crescent body 55 and tube 55 to pivot about the fulcrum and engaging the pawl 50 with the guide bar teeth 20. When pressure is applied to compress the spring 54, the locking member 40 pivots about the fulcrum, causing the pawl 50 to rise above and disengage the guide bar teeth 20. While the pawl 50 is disengaged from the guide bar teeth 20, the body 15 can freely slide along the guide bar 19.

As shown in FIGS. 2 and 4, the teeth 20 of the guide bar 19 have a sloped face facing the second anchor engaging element 14 and a generally perpendicular face facing the first anchor engaging element 12. As shown in FIG. 5, the pawl 50 has a tip with a generally perpendicular face facing the second anchor engaging element 14 and a sloped face facing the first anchor engaging element 12. Thus while the pawl 50 is engaged with teeth 20, applying a force to expand the first anchor engaging element 12 and second anchor engaging element 14 causes the pawl 50 to slide up the sloped side of an individual tooth 20, overcoming the resistance provided by the spring 54. Because the perpendicular faces of the teeth 20 and pawl 50 engage when a force is applied to contract the first anchor engaging element 12 and the second anchor engaging element 14, movement is prevented in that direction.

When the first anchor engaging element 12 and the second anchor engaging element 14 are moved apart and held by the locking member 40, the anchor engaging arms 18 are also held in position. When engaged with anchors (for example, bone screws) positioned in a pair of vertebrae, the engagement arms 18 will distract and hold the vertebrae a desired distance apart, allowing access to the disc space between them.

According to one example, the spinal distraction assembly 10 can be used to accomplish the distraction of adjacent vertebrae by first accessing at least a portion of each vertebra through either of an open or minimally invasive operative corridor and implanting an anchor member in each vertebra. By way of example only, the anchors may be pedicle screws implanted through the vertebral pedicles. Once the anchors are implanted the distraction assembly 10 may be inserted through the operative corridor and the engaging arms 18 may be positioned next to the anchors. Force may then be applied to the spinal distraction assembly 10 so that it applies a distraction force to the vertebral anchoring members, separating the vertebrae to the desired position. By way of example, force may be applied with any number of suitable instruments (e.g. scissor-type spreaders, etc. . . . not shown) that may engage the inner sides of arms 18 and spread them apart. At this point the anchor engaging arms 18 will act on the anchors to hold the disc space in the distracted position as long as desired. For example, with the distraction device 10 in position, the disc space may be prepared using general disc space preparation tools and techniques and an implant (e.g. fusion implant or disc replacement) may be positioned in the disc space. With the implant positioned, the locking member 40 may be disengaged and the distraction assembly 10 may be moved back to a contracted position. The disc space may then collapse to the size of the implant which should maintain the disc space at the appropriate height. The anchor elements may also be connected with a connecting element, such as a spinal rod, to fix the vertebrae relative to each other.

FIGS. 6-9 illustrate, according to a second example embodiment, a spinal distraction assembly 110. Similar to the first example embodiment described above, the vertebral distraction assembly 110 includes a first anchor engaging element 112 and a second anchor engaging element 114. First anchor engaging element 112 includes a body 115 having a channel extending through the longitudinal axis of the body. Second anchor engaging element 114 includes a guide bar 119. Guide bar 119 is dimensioned to slide through the body channel. Anchor engaging arms 118 extend approximately 90° laterally from each of the body 115 and guide bar 119. A locking element 117 is configured to engage the guide bar 19 and lock the position of body 115 relative to guide bar 119.

The first anchor engaging element 112 and the second anchor engaging element 114 interconnect so that the body 115 of the first anchor engaging elements receives the guide bar 119 of the second anchor engaging element 114 therethrough. The body 115 is movable along the guide bar 119 to either expand or contract the distance between the anchor engaging arms 118. When the anchor engaging arms 118 are engaged with anchors implanted in a pair of vertebral bodies, operating the distraction assembly 110 to expand the distance between the anchor engaging arms will distract the disc space between the vertebral bodies. Likewise, operating the distraction assembly 110 to contract the distance between the anchor engaging arms 118 when the arms 118 are engaged with anchors implanted in a pair of vertebral bodies, the disc space between the bodies will be compressed.

By way of example only, the guide bar 119 may be generally rectangular and dimensioned to translate within a generally rectangular channel extending through body 115. Although guide bar 119 is described in the present embodiment as having a generally rectangular shape configured to fit within body 115, other suitable configurations are also possible, for example, the guide bar 119 can be generally cylindrical or partially cylindrical and the body 115 can have a generally cylindrical or partially cylindrical channel that the guide bar 119 can slide through.

Figure 7:
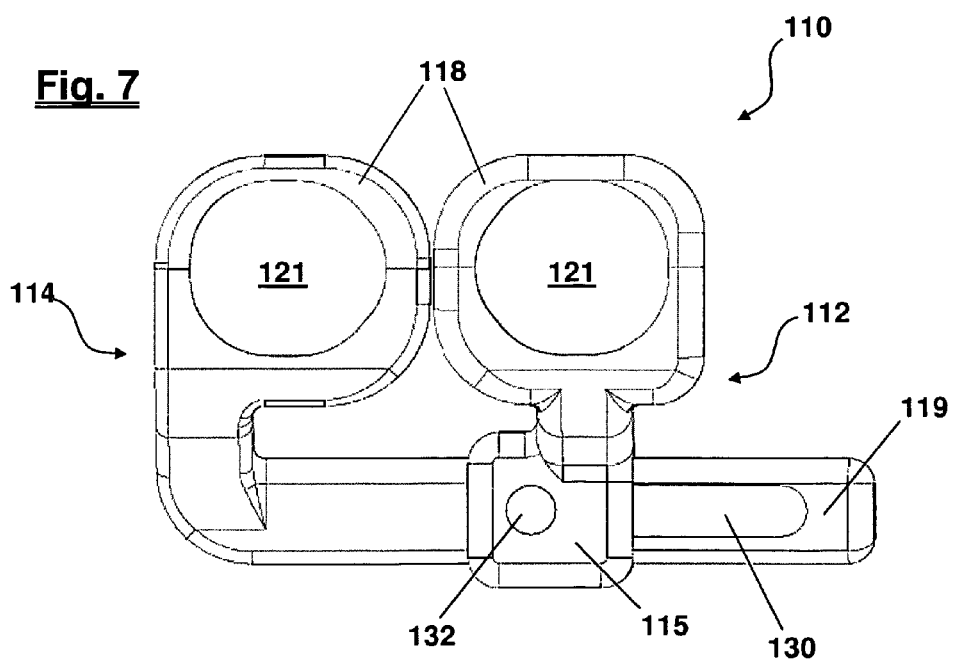
FIG. 7 is a bottom view of the vertebral distraction assembly of FIG. 6.

FIG. 7 illustrates the bottom of the spinal distraction assembly 110. The bottom of the guide bar 119 includes a groove 130 that runs lengthwise along the longitudinal axis of the guide bar 119. The groove 130 engages a protuberance 132 (best illustrated in FIGS. 8 and 9) on the body 115 which projects inward into the groove 130. The groove 130 extends along the length of the back of guide bar 119, but terminates before the end of the guide bar 119 such that the body 115 can slide out to a position near the end of the guide bar 119, but is prevented from sliding off the guide bar 19 and separating from the second anchor engaging element 114. When the body 115 slides out to the end of the guide bar 119 such that the protuberance 132 reaches the end of the groove 130, the spinal distraction assembly 10 is distracted at its maximum distance.

The first anchor engaging element 112 and the second anchor engaging element 114 each include an anchor engaging arm 118 that extends laterally at a generally 90° angle away from the body 115 and guide bar 119, respectively. According to this example embodiment, the anchor engaging arms 118 terminate in a looped end with apertures 121 intended to engage anchor elements implanted into adjacent vertebrae. According to FIGS. 6 and 7, apertures 121 are generally circular in shape such that when engaged with vertebral anchors, anchor engaging arms 118 cannot be disengaged from the anchors without lifting the distraction assembly 210 away from the bone anchors. According to one example, the apertures may be dimensioned to advance over the shaft of an anchor element, such as for example, a pedicle screw. This may be useful for example where the pedicle screw is of the variety where the bone anchor is implanted into the pedicle first and the receiver member is connected to the bone anchor thereafter. Alternatively, the apertures 121 may be dimensioned such that they may be advanced over the larger receiver member.

FIGS. 8 and 9 illustrate a perspective view of the first anchor engaging element 112. In this example, the locking element 17 includes a set screw 123 and a threaded aperture 124. The set screw 123 has a head portion 125 and a threaded screw portion 127. Head portion 125 has a generally hexagonal shape (by way of example only) configured to engage a driver instrument (not shown) such that a rotational force may be applied to set screw 123. Located on the top of body 115 is threaded aperture 124 having a threaded interior in communication with threaded screw portion 127. When fully engaged, the set screw 123 maintains a compression force on the guide bar 119 such that movement of the guide bar 119 within the body 115 is inhibited.

As best illustrated in FIG. 9, the set screw 123 has a threaded screw portion 127 in communication with the threaded aperture 123. A clockwise turn of set screw 123 advances the set screw 123 in a direction towards the guide bar 119, and a counterclockwise turn of set screw 123 withdraws the screw 123 in a direction away from the guide bar 119. When the set screw 123 is not engaged with the guide bar 119, the body 115 is free to translate along the guide bar 119 in both directions. When the set screw 123 is fully engaged with the guide bar 119, a compressive force is applied to the guide bar 119 such that translation of the body 115 is inhibited and the guide bar 119 is locked in place.

When the first anchor engaging element 112 and the second anchor engaging element 114 are moved apart and held by the set screw 123, the anchor engaging arms 18 are also held in position. When engaged with anchors (for example, bone screws) positioned in a pair of vertebrae, the engagement arms 118 will distract and hold the vertebrae a desired distance apart, allowing access to the disc space between them.

According to one example, the spinal distraction assembly 110 may be used in similar fashion to the spinal distraction assembly 10. That is, the spinal distraction assembly 110 can be used to accomplish the distraction of adjacent vertebrae by first accessing at least a portion of each vertebra through either of an open or minimally invasive operative corridor and implanting an anchor member, for example, a pedicle screw, in each vertebra. Once the anchors are implanted, the distraction assembly 110 may be inserted through the operative corridor and the engaging arms 118 may be advanced over the anchor members such that the anchors are received in the apertures 121. Force may then be applied to the spinal distraction assembly 110 so that it applies a distraction force to the vertebral anchoring members, separating the vertebrae to the desired position. When the desired distraction is achieved the set screw 123 may be advanced into contact with the guide bar 119 to lock the distraction position. By way of example, force may be applied with any number of suitable instruments (e.g. scissor-type spreaders, etc. . . . not shown) that may engage the inner sides of arms 18 and spread them apart. At this point the anchor engaging arms 118 will act on the anchors to hold the disc space in the distracted position as long as desired allowing access to the disc space, for example, to prepare and deliver an implant as discussed above. When the distraction is no longer desired the spinal distraction assembly 110 can be removed withdrawing the set screw 123 such that the compressive force on the guide bar 119 is released, and disengaging the anchor engaging arms 118 from the anchor members.

FIGS. 10-16 illustrate still another example embodiment of spinal distraction assembly 210. Similar to the previous embodiments described above, the present embodiment includes a first anchor engaging element 212 and a second anchor engaging element 214. First anchor engaging element 212 includes a body 215 having a channel extending through the longitudinal axis of the body. Second anchor engaging element 214 includes a guide bar 219. Guide bar 219 is dimensioned to translate through the body channel. Anchor engaging arms 218 extend approximately 90° laterally from each of the body 215 and guide bar 219. The vertebral distraction assembly 210 also includes an adjustor 216 operable to translate the body 215 relative to the guide bar 219.

The first anchor engaging element 212 and the second anchor engaging element 214 interconnect so that the body 215 of the first anchor engaging elements receives the guide bar 219 of the second anchor engaging element 14 therethrough. The body 21 is movable along the guide bar 219 to either expand (distract) or contract (compress) the distance between the anchor engaging arms 218. When the anchor engaging arms 218 are engaged with anchors implanted in a pair of vertebral bodies, operating the distraction assembly 210 to expand the distance between the anchor engaging arms will distract the disc space between the vertebral bodies. Likewise, operating the distraction assembly 210 to contract the distance between the anchor engaging arms 218 when the arms 218 are engaged with anchors implanted in a pair of vertebral bodies, the disc space between the bodies will be compressed.

The first anchor engaging element 212 and the second anchor engaging element 214 each include an anchor engaging arm 218 that extends laterally at a generally 90° angle away from the body 215 and guide bar 219, respectively. According to this example embodiment, the anchor engaging arms 218 terminate in a looped end with apertures 221 intended to engage anchor elements implanted into adjacent vertebrae. Apertures 221 may be generally circular in shape such that when engaged with vertebral anchors, anchor engaging arms 218 cannot be disengaged from the anchors without lifting the distraction assembly 210 away from the bone anchors. According to one example, the apertures may be dimensioned to advance over the shaft of an anchor element, such as for example, a pedicle screw. This may be useful for example where the pedicle screw is of the variety where the bone anchor is implanted into the pedicle first and the receiver member (for receiving and locking a connecting rod) is connected to the bone anchor thereafter. Alternatively, the apertures 221 may be dimensioned such that they may be advanced over the larger receiver member portion of the pedicle screw.

FIG. 12 illustrates the bottom of the spinal distraction assembly 210. The bottom of the guide bar 219 includes a groove 230 that runs lengthwise along the longitudinal axis of the guide bar 219. The groove 230 engages a protuberance 232 (best illustrated in FIG. 12) on the body 215 which projects inward into the groove 230. The groove 230 extends along the length of the back of guide bar 219, but terminates before the end of the guide bar 219 such that the body 215 can move out to a position near the end of the guide bar 219, but is prevented from moving off the guide bar 219 and separating from the second anchor engaging element 214. When the body 215 slides out to the end of the guide bar 219 such that the protuberance 232 reaches the end of the groove 230, the spinal distraction assembly 210 is distracted at its maximum distance.

According to the present embodiment, the distraction assembly 210 has an adjustor 216. With reference to FIGS. 13-16, the adjuster 216 may be generally ring shaped and includes an inner bore 270 defining a rotational axis R1 coaxial with the longitudinal axis of the guide bar 219. The inner bore 270 is dimensioned to snugly pass the guide bar 219 therethrough. The interior surface of the inner bore 270 may include threading 269 complementary to the guide bar threading 226 such that rotation of the adjuster 216 about the guide bar 219 causes the adjuster 216 to translate along the longitudinal axis of the guide bar 219. The adjuster 216 is further coupled to the body 215 such that the adjuster 216 is longitudinally fixed relative to the body 215 but is freely rotatable relative to the body 215. Thus, as the adjuster 216 is rotated about the guide bar 216 the adjuster moves longitudinally along the guide bar 219 and drives the body 215 along the guide bar 219 in the same direction.

The coupling of the adjuster 216 to the body 215, according to one example, may best be appreciated with reference to FIGS. 14-16. The body 215 is provided with an extension member 276. Extension member 276 includes a groove 278 and a ridge 280. The adjuster 216 is also provided with a groove 263 and a ridge 265. The groove 263 and ridge 265 are situated along the interior of adjuster 216 and are complementary to the ridge 280 and groove 278 of extension member 276. When coupled, the ridge 280 of the extension member 276 is captured in the groove 263 of the adjuster 216 and the ridge 265 of the adjuster 216 is captured in the groove 278 of the extension member. Thus the adjuster 216 is free to rotate about the axis R2 while remaining longitudinally fixed to the body 215. A washer 267 may be disposed between the body 215 and adjuster 216 to maintain a snug fit. A distraction tool 310, described below may be used to impart rotation on the adjuster 216.

Figure 26:
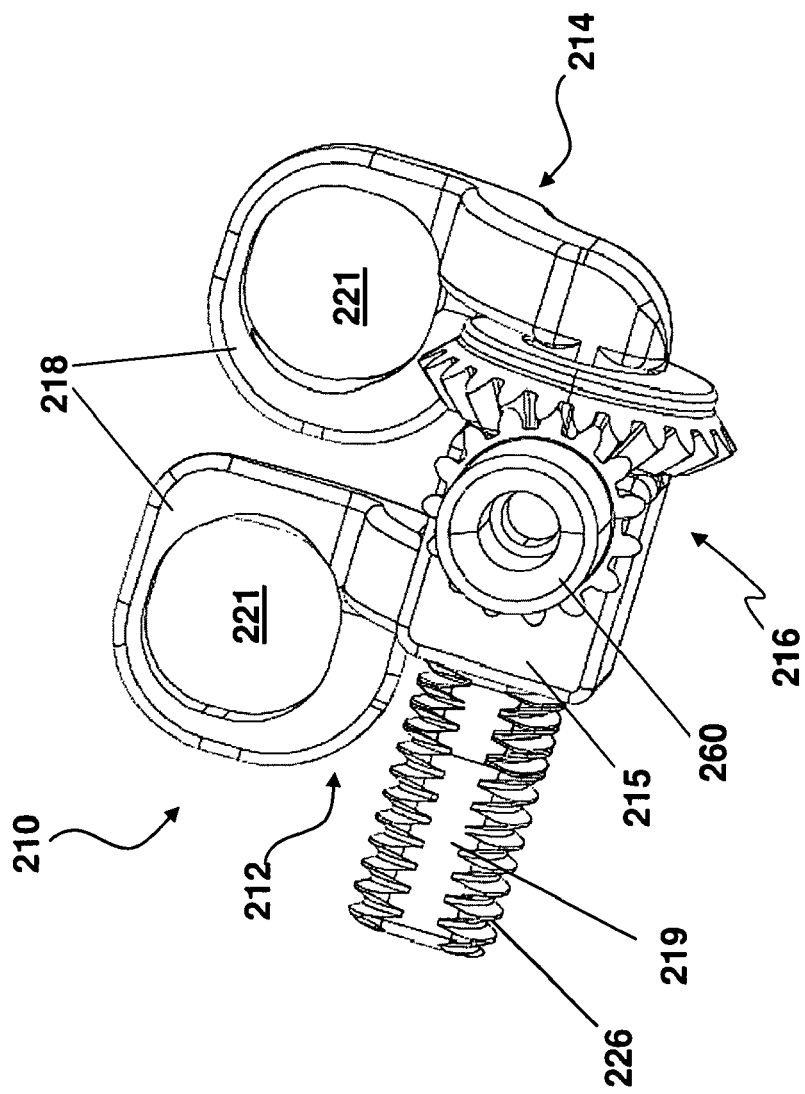
FIGS. 26-27 illustrate an alternate embodiment of a vertebral distraction assembly, according to another example embodiment.
Figure 27:
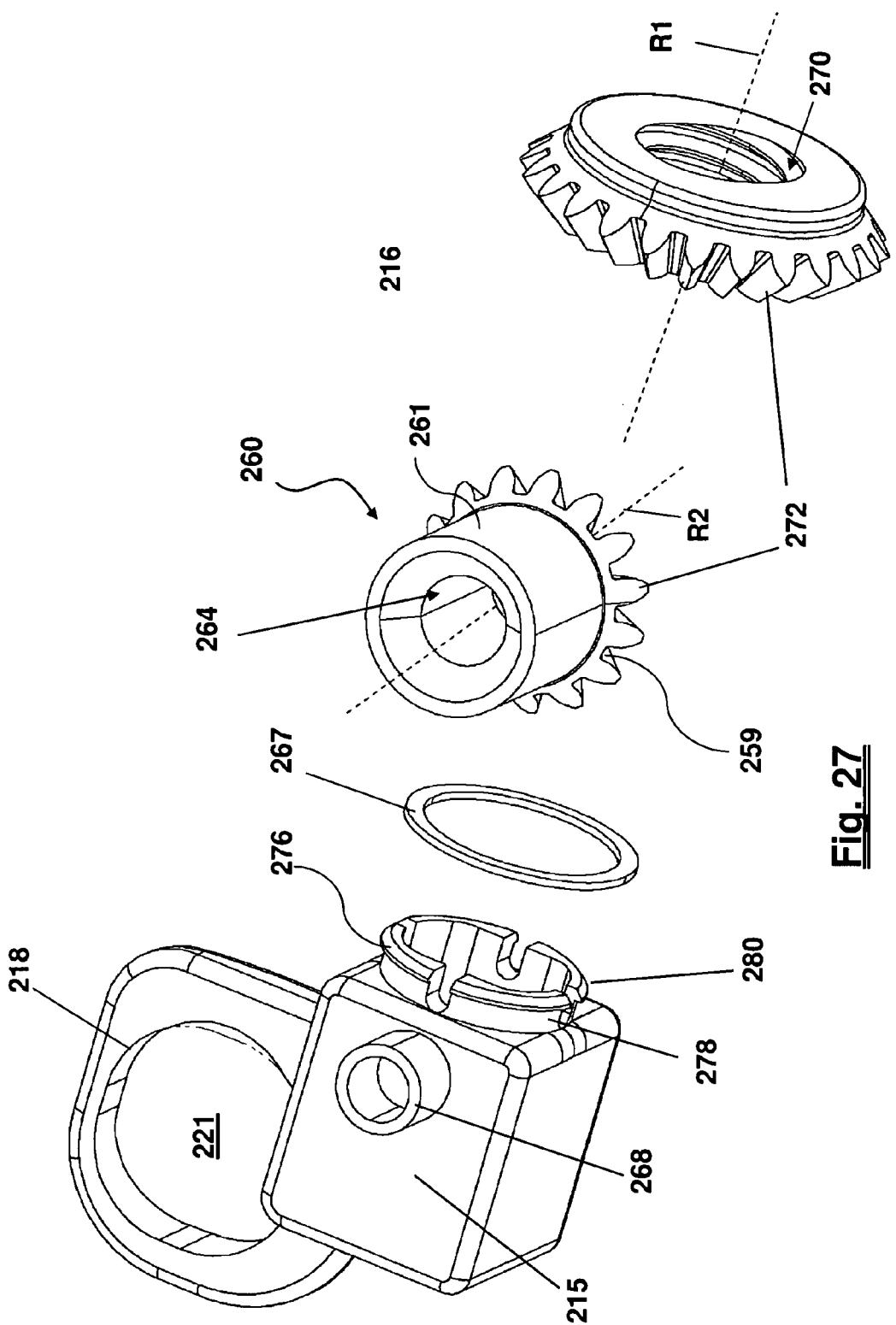

In an alternate embodiment shown in FIGS. 26-27, the distraction assembly 210 includes an additional transition wheel 260 impart rotational force to the adjuster 216. As best illustrated in FIG. 14, transition wheel 260 is generally cylindrical in shape and has a body portion 261, a gear portion 259, and an inner bore 264 extending therethrough and defining a rotational axis R2 of the transition wheel 260. The transition wheel 260 is attached to the body 215 via wheel post 268 that extends up from the body 215 perpendicular to the longitudinal axis of the body channel (and guide bar 219). The wheel post 268 is received within the inner bore 264 such that the wheel post is coaxial with the rotation axis R2 and the transition wheel 260 may rotate around the wheel post 268. The gear portion 259 is located at the base of transition wheel 260 and includes teeth 272 surrounding the exterior of gear portion 259. The teeth 272 project out from the body 261 at an oblique angle to the rotational axis R1. The adjuster 216 also includes teeth 273. The teeth 273 project out from adjuster 216 at an oblique angle to the rotational axis R2 and engage with the teeth 272 of transition wheel 260 such that rotation of the transition wheel 260 about the axis R2 causes rotation of the adjuster 216 about the axis R1.

Thus the user may apply a apply a rotational force to transition wheel 60 which will cause the adjuster 216 to rotate about the guide bar 219 such that the threading 269 of the adjuster will advance along the guide bar threading 226 driving the body 215, and hence the first anchor engaging element 12 in the same direction. By way of example only, rotating the transition wheel 260 counter clockwise may drive the body 215 along the guide bar 219 to expand the distance between the engaging arms 218, distracting the disc space when the anchor engaging arms are engaged to anchor members implanted in the vertebrae. Conversely, and by way of example only, a clockwise rotation of transition wheel 60 will drive body 215 along the guide bar 219 to contract the distance between the two anchor engaging arms 18 and consequently compress the disc space.

FIGS. 17-24 illustrate one example embodiment of a distraction tool 310 for use with the spinal distraction assembly 210. By way of example only, distraction tool 310 includes a proximal handle 311, a medial handle 312, a distal handle 313, a distal engagement region 314, and an elongated first shaft 315. As best illustrated in FIGS. 18 and 20, distal engagement region 314 includes a plurality of engagement arms 316, and a housing 320. Engagement arms 316 are composed of a base member 321 and an extension member 322 connected by a hinged connector 319. The engagement arms 316, and particularly the extension members 322, are sized and dimensioned to securely grasp the body 215 of the spinal distraction assembly 210.

The opening (lateral direction) and closing (medial direction) of the engagement arms 316 can be performed by rotating the medial handle 312. The medial handle 312 is fixed to a threaded coupler 370 which has threaded features (not shown) in its inside diameter. The threaded features of the coupler 370 are engaged with the threaded features (not shown) on the outside diameter and proximal end 181 of the elongated second shaft 380. At the distal end 382 of the elongated second shaft 380, the base member 321 is attached. Therefore, when the medial handle 312 is rotated, it causes the threads of the coupler 370 to rotate (best viewed in FIG. 22) which forces the second shaft 380 to travel linearly along its central axis and force the base members 321 to move. Movement of base members 321 and the configuration of the hinge connectors 319 force the movement of extension members 322 in either direction (open or closed). The direction of travel of the second shaft 380 depends on the direction of rotation of the medial handle 312 and the direction of the threaded features. By way of example only, a clockwise turn of the medial handle 312 can result in the movement of the engagement arms 316 to an open position due to the advancement of the second shaft 380 in the direction of its distal end 382. A set screw 330 (shown in FIG. 17) through the medial handle 312 engages an annular groove 331 (best viewed in FIG. 23) at the proximal end 332 of the distal handle 313 which allows the medial handle 312 to rotate freely while fixing its longitudinal position at the proximal end 332 of the distal handle 313.

The distal handle 313 is permanently fixed at its distal end 333 to the proximal end of the first shaft 315 which is permanently fixed at its distal end to the housing 320, with both of these connections preventing longitudinal and rotational movement relative to each other. The partial function of the distal handle 313 is to provide a grasping area for the user.

Figures 21, 22:
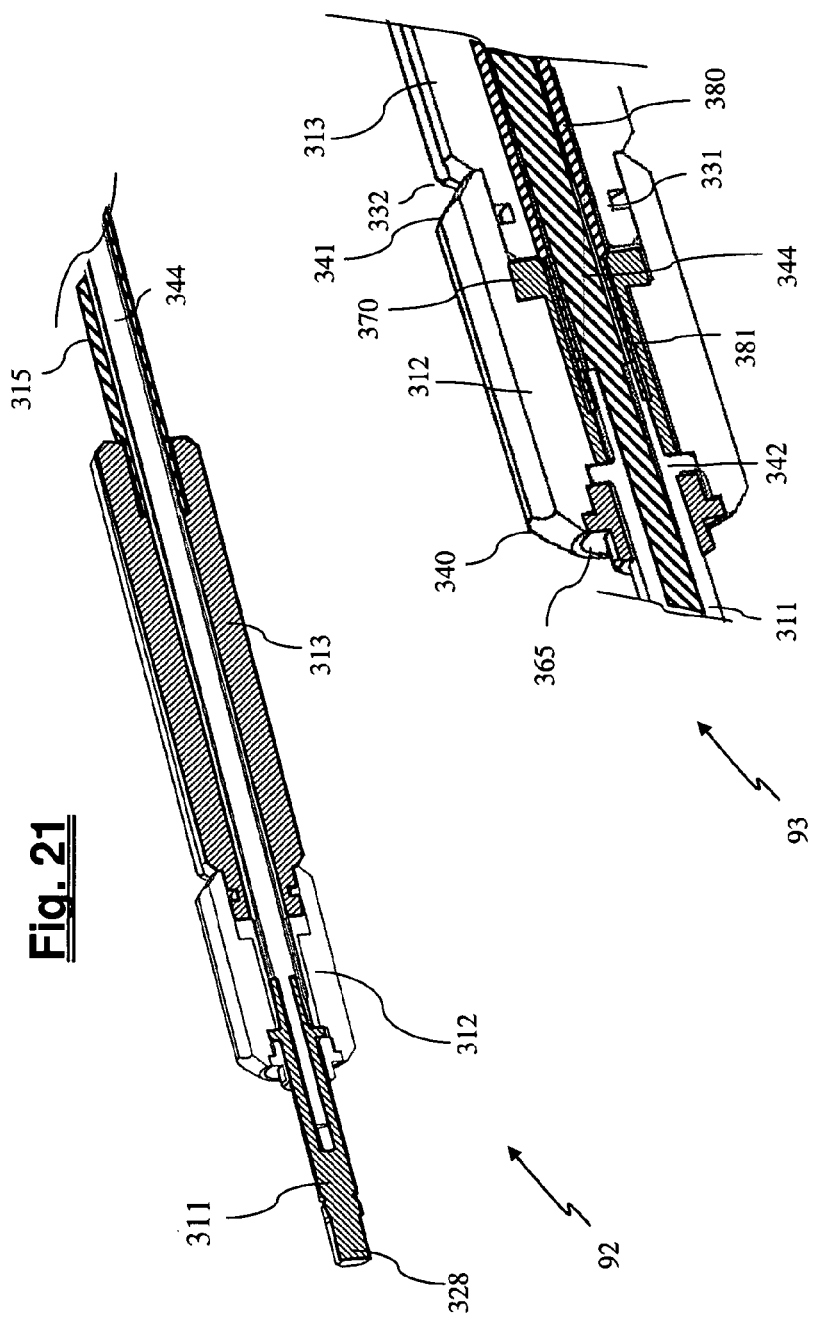
FIG. 21 is a perspective cross-section view of a distal handle region of the distraction tool of FIG. 17.
FIG. 22 is a perspective cross-section view of an intermediate handle of the distal handle region of FIG. 21.
Figure 28:
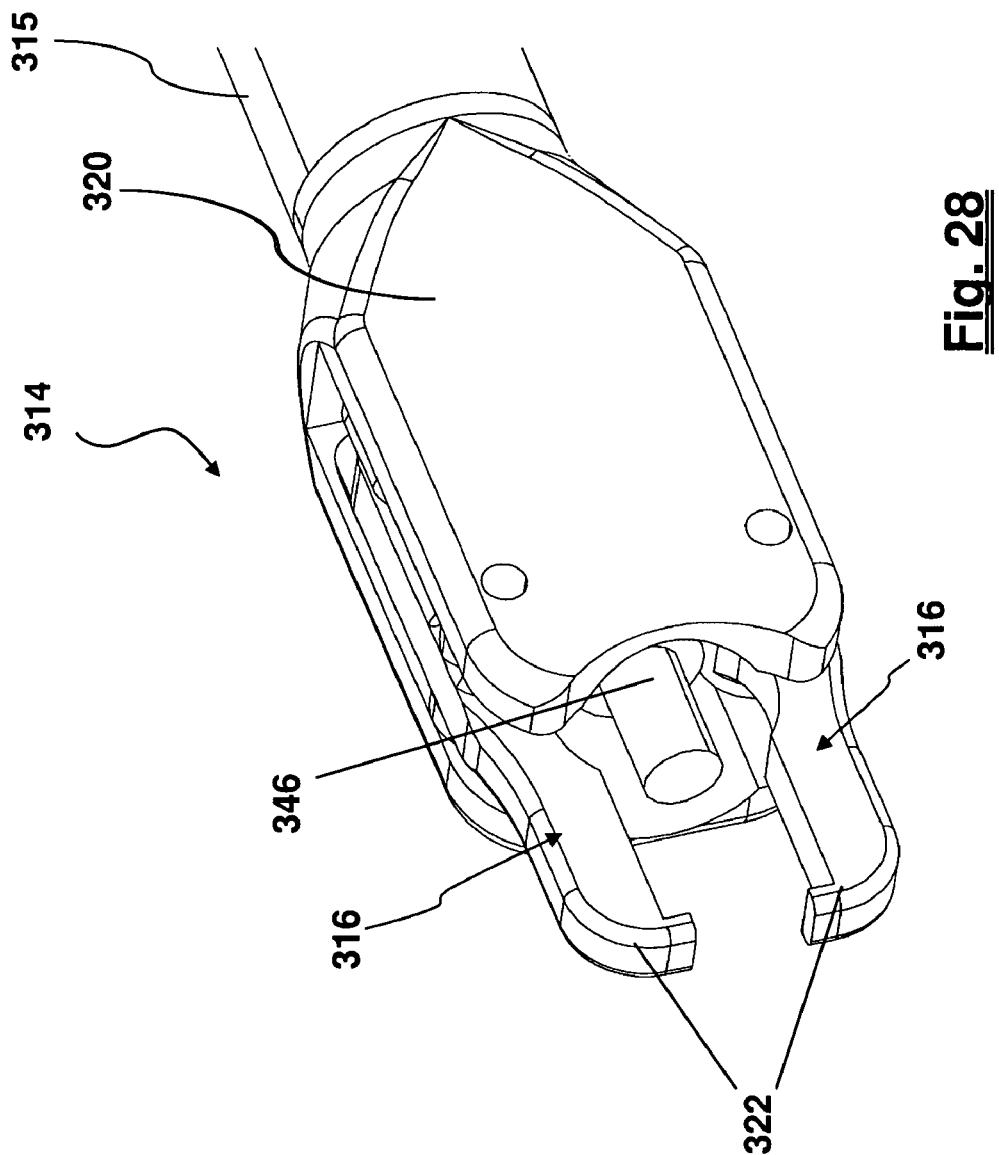
FIG. 28 is a perspective view of the distal end of distraction tool 310, according to another example embodiment.

As best illustrated in FIGS. 21 and 22, the proximal handle 311 can rotate about its center axis and can do so independently from the medial handle 312, and vice versa. The end cap 365 is secured into the proximal end 340 of the medial handle 312 and one of its functions is to secure the proximal handle 311 to the proximal end 340 of the medial handle 312. An adapter feature 328 at the proximal end 343 of the proximal handle 311 enables tools (e.g. t-handles, etc. . . . —not shown) to couple to the adapter feature 328. Extending rigidly from approximately the center of the distal end 342 of the proximal handle 311 is the third shaft 344. As best illustrated in FIGS. 18 and 20, third shaft 344 extends to the distal engagement region 314. At the distal end of third shaft 344 is an engagement member 347. By way of example only, engagement member 347 may be a gear configured to engage the adjuster 216 such that rotating the proximal handle 311 causes the gear to rotate which in turn rotates the adjuster 216. The gear 347 is similar to the transitional wheel described above and engages the adjuster in the same manner. engages the adjuster in the same manner. An alternate embodiment of the tool 310 is illustrated in FIG. 28. In the embodiment shown in FIG. 28, an engagement member 346 replace engagement member 347 and may be configured to fit within the inner bore 264 of transition wheel 260 such that the distraction tool 310 may apply a rotational force to transition wheel 260, driving body 215 along the guide bar 219 and adjusting the distance between the anchor engaging arms 218.

Figure 23:
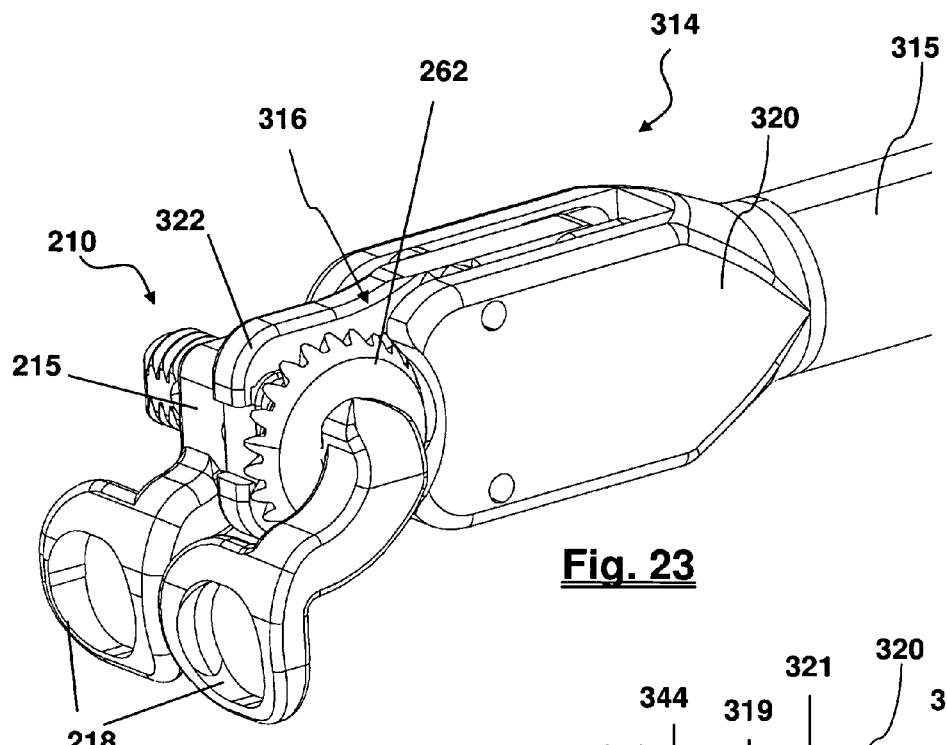
FIG. 23 is a perspective view of the distal end of the spinal distraction assembly of FIG. 10 coupled with the distraction tool of FIG. 17.
Figure 24:
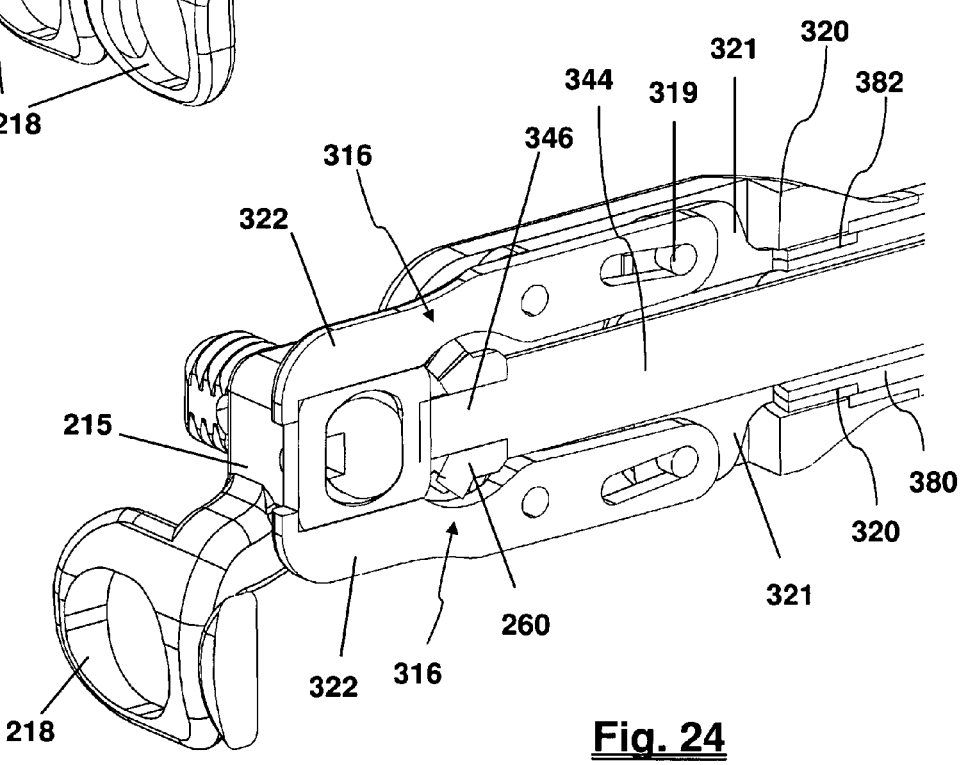
FIG. 24 is a cross section view of the spinal distraction assembly of FIG. 10 coupled with the distraction tool of FIG. 17.

FIGS. 23 and 24 illustrate distraction tool 310 engaged with spinal distraction assembly 210. By way of example only, extension members 322 are configured to snugly fit around the body 215 to prevent rotation and movement of spinal distraction assembly 210. As illustrated in FIG. 24, rotation of third shaft 344 causes the cause gear 347 to rotate the adjuster 216 and allows the user to distract the distance between anchor engaging arms 218 (as explained above) by rotating the proximal handle 311.

Figure 25C:
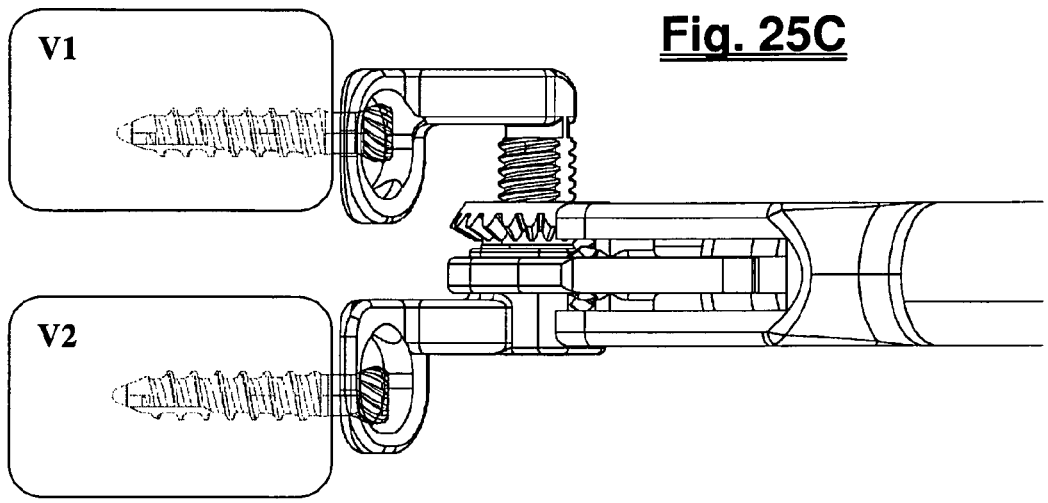
Figure 25D:
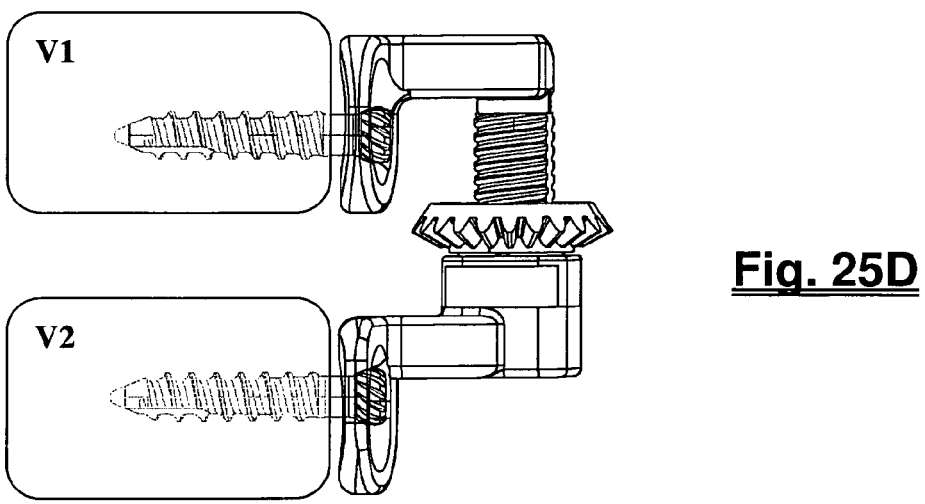
Figure 25E:
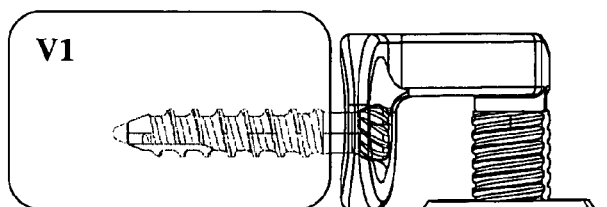

According to one example usage, and with reference to FIGS. 25A-25E the spinal distraction assembly 210 can be used to accomplish the distraction of adjacent vertebrae and increase access to the disc space by first accessing at least a portion of each vertebra through either of an open or minimally invasive operative corridor and implanting an anchor member in each vertebra, shown in FIG. 25A. The bone anchor 402 shown in FIG. 25A comprises the anchor portion of a pedicle screw 400 that includes bone anchor 402 and a receiving member 404 that may be attached to the head of the bone anchor after the bone anchor is implanted. It should be appreciated however, the distraction assembly 210 may be used with other anchor members as well. By way of example only, the anchors may be pedicle screws in which the receiving member 404 initially attached to the bone anchor. This may be accomplished, by way of example, providing larger anchor engaging arms 218 and increasing the size of the aperture 121.

Turning to FIG. 25B, once the anchors are implanted, the distraction assembly 10 may be attached to the distraction tool 310 by positing the engaging arms 316 about the body 215 and rotating the medial handle 312 to securely grasp the distraction assembly 210. Using the distraction tool 310 the distraction assembly may then be inserted through the operative corridor to the target site. The apertures 121 of engaging arms 218 are advanced over the bone anchors 402, as in FIG. 25B. With the anchor engaging arms 218 properly positioned, the adjuster 216 may be operated to advance the body 215 along the guide track 219, forcing apart the anchor engaging arms 218 and hence the bone anchors 402 and the vertebra they are implanted in (FIG. 25C). This may be accomplished by rotating the proximal handle 311 which will in turn impart rotation to the transition wheel 260 which is engaged with the adjuster 216, causing the adjuster to rotate about the guide bar 219. When the desired distraction height has been achieved, the distraction tool may be removed from the distraction assembly by rotating the medial handle 312 in opposite direction it was turned to engage the implant. The distraction assembly 216 will maintain the distraction height until the assembly is removed.

Figure 25F:
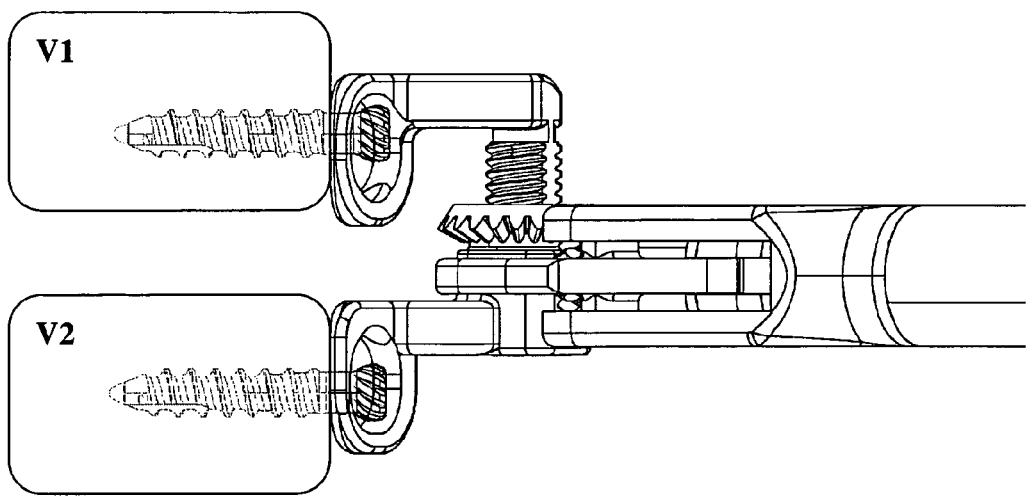
Figure 25G:
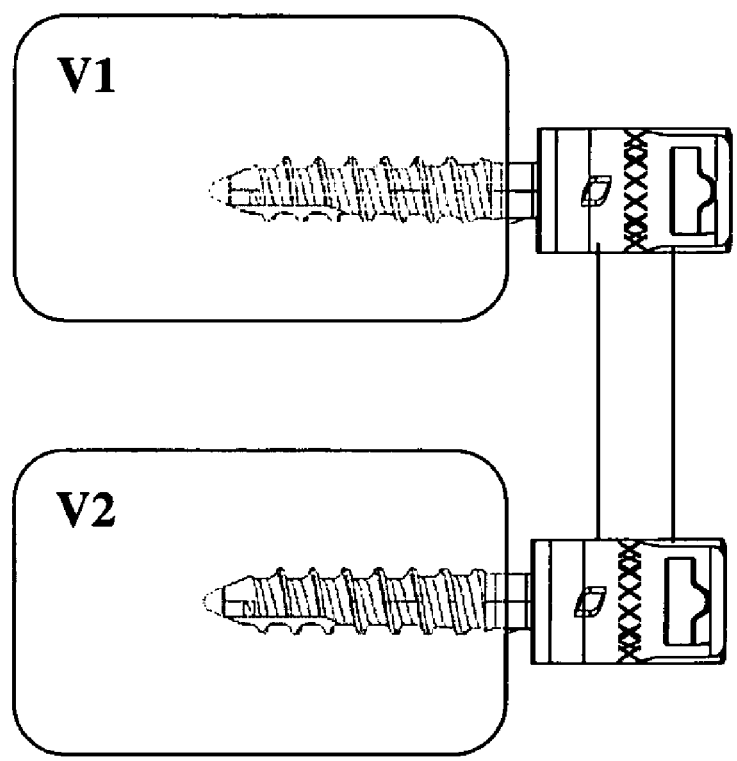

With the distraction assembly 216 engaged to the bone anchors 402 (FIG. 25D) the distracted disc height may be maintained without the encumbrances of having distraction tools taking up space in the operative corridor and/or a portion of the disc space. At this point the surgeon may perform the desired procedure in the disc. By way of example only, the surgeon may perform a procedure to fuse the adjacent vertebrae. As pictured in FIG. 25E, the disc space may be prepared using general disc space preparation tools and techniques and a fusion implant 406 may be positioned in the disc space. It will be appreciated that while this procedure is being described as a fusion procedure, other non-fusion implants, including, but not necessarily limited to disc replacements, etc . . . , may be implanted instead. With the implant positioned in the disc space and adapted to maintain the desired disc height, the distraction assembly may be removed. This can be accomplished by inserting the distraction tool 310 through the operative corridor and reengaging the engaging arms 316 to the body 215 (FIG. 25F). If necessary, the proximal handle 311 may be rotated to contract the engaging arms 218 until the distraction assembly can be removed. Once the distraction assembly is removed from the operative corridor the receiving members 404 may be attached to the respective bone anchors 402. A connecting element 408 may be fixed to each anchor member 400 to stabilize or fix the vertebra relative to each other (FIG. 25G.). The connecting element 408 may be a rigid rod or a dynamic rod. To complete the procedure, the operative corridor is closed.

While this invention has been described in terms of a best mode for achieving this invention's objectives, it is understood by those skilled in the art that variations may be accomplished in view of these teachings without deviating from the spirit or scope of the invention. Moreover, the various embodiments disclosed herein are provided by way of example only, and the specific features described in relation to the specific embodiments are not limited to those specific embodiments, but rather may be provided interchangeably and in combination with any of the various features disclosed herein without departing from the scope of the present invention.

What is claimed is:

1. A spinal distraction system for distracting a space between a first vertebra and a second vertebra wherein the first vertebra has a bone anchor implanted therein and the second vertebra has a second bone anchor implanted therein, comprising:
    a distraction assembly comprising:
        a first anchor engaging element having a body portion with a first bore extending therethrough and a first anchor engaging arm extending from said body and configured to engage said first bone anchor, said body portion including a pair of grooves;
        a second anchor engaging element having a guide bar dimensioned to be received within said first bore and having a second anchor engaging arm extending from said guide bar and configured to engage said second bone anchor, said guide bar defining a longitudinal axis;
        an adjuster having a first gear and a second bore coaxial with the first bore on said body portion and situated around the guide bar, the adjuster being attached to the body portion such that the adjuster is freely rotatable relative to the body portion and longitudinally fixed to the body portion, wherein rotation of the adjuster around said guide bar causes said body portion to move from one position on said guide bar to another position on said guide bar; and
    a distraction tool that releasably engages said distraction assembly to operate said adjuster and move said body portion from one position on said guide bar to another position on said guide bar, wherein the distraction tool includes a pair of arms that grasp said pair of grooves on said body portion and a second gear mateable with said first gear.

2. The spinal distraction system of claim 1, wherein said guide bar includes an exterior thread along at least a portion of the length of said guide bar.

3. The spinal distraction system of claim 2, wherein said second bore includes an internal thread complementary to said external thread of said guide bar and wherein rotating said adjuster about said guide bar causes said adjuster to threadedly translate along said guide bar.

4. The spinal distraction system of claim 2, wherein said guide bar includes a groove extending lengthwise along the longitudinal axis and said body includes a protuberance extending into said groove to prevent removal of said body from said guide bar.

5. The spinal distraction system of claim 1, wherein said first anchor engaging arm and said second anchor engaging arm have loop ends.

6. The spinal distraction system of claim 5, wherein said loop end of said first anchor engaging arm and said loop end of said second anchor engaging arm are dimensioned to pass a shaft of a bone anchor.

7. The spinal distraction system of claim 6, wherein said loop end of said first anchor engaging arm and said loop end of said second anchor engaging arm are dimensioned to pass a receiving element of a bone anchor.

8. The spinal system of claim 1, wherein said pair of arms are adjustable between a first position in which the pair of arms tightly grasp said body and a second position in which said pair of arms do not grasp said body.

9. The spinal distraction system of claim 8, wherein said second gear is situated between said pair of arms.

10. The spinal distraction system of claim 9, wherein said distraction tool includes a first shaft that moves to adjust the position of said pair of arms and a second shaft that moves to operate said second gear.

11. The spinal distraction system of claim 10, wherein said second shaft is disposed through a passageway in said first shaft.

12. A spinal distraction system for distracting a space between a first vertebra and a second vertebra wherein the first vertebra has a bone anchor implanted therein and the second vertebra has a second bone anchor implanted therein, comprising:
    a distraction assembly comprising:
        a first anchor engaging element having a body with a first bore extending therethrough and a first anchor engaging arm extending from said body and configured to engage said first bone anchor;
        a second anchor engaging element having a guide bar dimensioned to be received within said first bore and having a second anchor engaging arm extending from said guide bar and configured to engage said second bone anchor, said guide bar defining a longitudinal axis;
        an adjuster having a first gear and a second bore coaxial with the first bore on said body and situated around the guide bar, the adjuster being attached to the body such that the adjuster is freely rotatable relative to the body and longitudinally fixed to the body, wherein rotation of the adjuster around said guide bar causes said body to move from one position on said guide bar to another position on said guide bar; and
    a distraction tool that releasably engages said distraction assembly to operate said adjuster and move said body from one position on said guide bar to another position on said guide bar, wherein said distraction tool includes a first shaft, a second shaft, a pair of arms adjustable between a first position in which the pair of arms tightly grasp said body and a second position in which said pair of arms do not grasp said body, and a second gear situated between said pair of arms and mateable with said first gear, wherein said first shaft moves to adjust the position of said pair of arms and the second shaft that moves to operate said second gear.

13. The spinal distraction system of claim 12, wherein said second shaft is disposed through a passageway in said first shaft.

14. The spinal distraction system of claim 12, wherein said guide bar includes an exterior thread along at least a portion of the length of said guide bar.

15. The spinal distraction system of claim 14, wherein said second bore includes an internal thread complementary to said external thread of said guide bar and wherein rotating said adjuster about said guide bar causes said adjuster to threadedly translate along said guide bar.

16. The spinal distraction system of claim 12, wherein said first anchor engaging arm and said second anchor engaging arm have loop ends.

17. The spinal distraction system of claim 16, wherein said loop end of said first anchor engaging arm and said loop end of said second anchor engaging arm are dimensioned to pass a shaft of a bone anchor.

18. The spinal distraction system of claim 17, wherein said loop end of said first anchor engaging arm and said loop end of said second anchor engaging arm are dimensioned to pass a receiving element of a bone anchor.

19. The spinal distraction system of claim 12, wherein said guide bar includes a groove extending lengthwise along the longitudinal axis and said body includes a protuberance extending into said groove to prevent removal of said body from said guide bar.

20. The spinal distraction system of claim 12, wherein said body includes a pair of grooves that receive said pair of arms.

* * * * *